US009783589B2

(12) United States Patent
Grewal et al.

(10) Patent No.: US 9,783,589 B2
(45) **Date of Patent: *Oct. 10, 2017**

(54) ENGINEERED ANTIBODY-INTERFERON FUSION MOLECULES FOR TREATMENT OF AUTOIMMUNE DISEASES

(71) Applicant: IMMUNGENE INC., Thousand Oaks, CA (US)

(72) Inventors: Iqbal Grewal, Chalfont, PA (US); Sanjay Khare, Palo Alto, CA (US); Michael Gresser, Ojai, CA (US)

(73) Assignee: IMMUNGENE INC, Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/421,657

(22) PCT Filed: Aug. 13, 2013

(86) PCT No.: PCT/US2013/054747
§ 371 (c)(1),
(2) Date: Feb. 13, 2015

(87) PCT Pub. No.: WO2014/028502
PCT Pub. Date: Feb. 20, 2014

(65) Prior Publication Data

US 2015/0203560 A1 Jul. 23, 2015

Related U.S. Application Data

(60) Provisional application No. 61/682,608, filed on Aug. 13, 2012.

(51) Int. Cl.

| | |
|---|---|
| ***C07K 16/00*** | (2006.01) |
| ***C07K 16/30*** | (2006.01) |
| ***C07K 16/46*** | (2006.01) |
| ***A61K 39/00*** | (2006.01) |
| ***A61K 39/395*** | (2006.01) |
| ***A61K 38/00*** | (2006.01) |
| ***A61K 38/21*** | (2006.01) |
| ***C07K 14/57*** | (2006.01) |
| ***C07K 14/555*** | (2006.01) |
| ***C07K 16/28*** | (2006.01) |
| ***C07K 14/56*** | (2006.01) |
| ***C07K 16/40*** | (2006.01) |

(52) U.S. Cl.
CPC ............ *C07K 14/57* (2013.01); *C07K 14/555* (2013.01); *C07K 14/56* (2013.01); *C07K 16/28* (2013.01); *C07K 16/2803* (2013.01); *C07K 16/2818* (2013.01); *C07K 16/2833* (2013.01); *C07K 16/2866* (2013.01); *C07K 16/2875* (2013.01); *C07K 16/2878* (2013.01); *C07K 16/2881* (2013.01); *C07K 16/2896* (2013.01); *C07K 16/40* (2013.01); *C07K 2317/24* (2013.01); *C07K 2317/54* (2013.01); *C07K 2317/55* (2013.01); *C07K 2317/622* (2013.01); *C07K 2317/624* (2013.01); *C07K 2317/626* (2013.01); *C07K 2319/00* (2013.01); *C07K 2319/33* (2013.01)

(58) Field of Classification Search
None
See application file for complete search history.

(56) References Cited

U.S. PATENT DOCUMENTS

2010/0172868 A1* 7/2010 Morrison ............. A61K 38/212 424/85.4
2011/0274658 A1* 11/2011 Silver .............. A61K 47/48276 424/85.7

OTHER PUBLICATIONS

Bork, 2000, Genome Research 10:398-400.*
Bork et al., 1996, Trends in Genetics 12:425-427.*
Wells, 1990, Biochemistry 29:8509-8517.*
Ngo et al., 1994, The Protein Folding Problem and Tertiary Structure Prediction, pp. 492-495.*
Wischhusen et al. (2002), Can. Res. vol. 62, pp. 2592-2599.*

* cited by examiner

*Primary Examiner* — Christine J Saoud
*Assistant Examiner* — Jegatheesan Seharaseyon
(74) *Attorney, Agent, or Firm* — Craig A Crandall

(57) ABSTRACT

The field of the present invention relates to genetically engineered fusion molecules, methods of making said fusion molecules, and uses thereof for treatment of autoimmune diseases. More specifically, the present invention provides novel genetically engineered fusion molecules comprising an interferon (IFN) molecule attached to an antibody (Ab) which targets an antigen which is differentially expressed or up-regulated on activated T cells as compared to resting T cells, wherein the fusion molecule when contacted to an activated T cell results in induced apoptosis and programmed cell death or impairment of functions of said activated T cell.

9 Claims, 3 Drawing Sheets

ENGINEERED ANTIBODY-INTERFERON FUSION MOLECULES FOR TREATMENT OF AUTOIMMUNE DISEASES

CROSS-REFERENCE TO RELATED APPLICATIONS

This application is a U.S. National Phase Application pursuant to 35 U.S.C. §371 of International Patent Application PCT/US2013/054747, filed Aug. 13, 2013, which claims priority to and benefit of U.S. Provisional Application No. 61/682,608, filed Aug. 13, 2012, which is incorporated herein by reference in its entirety for all purposes.

TECHNICAL FIELD

The field of the present invention relates to genetically engineered fusion molecules, methods of making said fusion molecules, and uses thereof in treatment of autoimmune diseases.

BACKGROUND ART

Autoimmune diseases are any diseases caused by immune cells that become misdirected toward healthy cells and/or tissues of the body, generally due to a breakdown of the body's mechanisms assuring the recognition of self from non-self. Autoimmune diseases are classified into two basic categories: antibody-mediated diseases such as systemic lupus erythematosus (SLE), pemphigus vulgaris, myasthenia gravis, hemolytic anemia, thrombocytopenia purpura, Grave's disease, Sjogren's disease and dermatomyositis; and cell-mediated diseases such as Hashimoto's disease, polymyositis, inflammatory bowel disease, multiple sclerosis (MS), diabetes mellitus, rheumatoid arthritis (RA), and scleroderma.

Apoptosis is an important mechanism in immune system regulation, responsible for elimination of autoreactive T-lymphocytes (T cells), B-lymphocytes (B cells) and monocytes from the circulation and prevention of their entry into the central nervous system (CNS). Recent studies have implicated apoptotic cell death pathways in initiating and propagating autoimmune diseases, as well as rendering individuals susceptible to such diseases (Mahoney and Rosen, Current Opinion in Immunology, 17:583-588, 2005). There is substantial evidence suggesting that autoreactive T cells which have deficiencies in their ability to undergo programmed cell death (i.e., failed apoptosis) are a primary culprit in many autoimmune disorders, including MS, RA and SLE. Id.

Interferon is an important cytokine which has multiple effects on the immune response (Theofilopoulos et al., Annu. Rev. Immunol., 23:307-336, 2005). Interferons include type 1 interferons (e.g., interferon-alpha (IFN-α) and interferon-beta (IFN-β)) and type 2 interferons (e.g., interferon-gamma (IFN-γ)). All type 1 IFNs are recognized by a shared receptor (IFN-αR) composed of two transmembrane proteins, IFN-αR1 and IFN-αR2. Immunomodulatory therapy with IFN-β has proven to be successful in reducing the severity of the underlying disease in patients with relapsing-remitting MS. FDA-approved IFN-β therapies for the treatment of relapsing-remitting MS in the United States include interferon β-1a (marketed as Avonex®, available from Biogen, Inc.), interferon-β-1b (marketed as Betaseron®, available from Chiron Corporation) and interferon β-1a (marketed as Rebif®, available from EMD Serono and Pfizer), having combined sales exceeding three billion dollars a year. Unfortunately, each of these therapeutic agents are only partially effective in reducing the frequency and severity of relapses, slowing the rate of disease progression, or reducing the degree of brain inflammation as measured by a variety of magnetic resonance imaging (MRI) techniques. There is a continuous need for more effective IFN-β products, as well as more efficient methods of making them.

Provided herein are the next generation of safer and more effective treatments for autoimmune diseases using genetically engineered fusion molecules comprising one or more IFN molecules attached to an antibody which has been specifically selected based on its ability to bind to a antigen determined to be a specific target antigen, and wherein the specific target antigen is determined to be differentially expressed or up-regulated on activated T cells as compared to resting T cells. Importantly, the engineered antibody-interferon fusion molecules of the present invention retain the potent cytotoxic effects of the IFN at optimum concentrations and with reduced systemic toxicities, thus improving the ability of the antibody-interferon fusion molecules to kill activated T cells and/or impair the functions of activated T cells, and thus providing for monoclonal antibody/IFN-based therapies having superior efficacy and safety profile for the treatment of autoimmune diseases.

DISCLOSURE OF THE INVENTION

In one aspect, the present invention provides novel genetically engineered fusion molecules comprising an interferon (IFN) molecule attached to an antibody (Ab) which targets an antigen which is differentially expressed or up-regulated on activated T cells as compared to resting T cells, wherein the fusion molecule when contacted to an activated T cell results in induced apoptosis and programmed cell death or impairment of functions of said activated T cell.

In various embodiments, the fusion molecule comprises a type 1 interferon. In various embodiments, the fusion molecule comprises a type 2 interferon. In various embodiments, the interferon is an interferon selected from the group consisting of IFN-α, IFN-β, and IFN-γ and fragments, modified forms, and mutant molecules thereof.

In various embodiments the IFN is attached to the antibody via a proteolysis resitant peptide linker. In various embodiments, the proteolysis resistant peptide linker is fewer than 15 amino acids in length. In various embodiments the proteolysis resistant linker is selected from the group consisting of SGGGGS (SEQ ID NO: 20) or AEAAAKEAAAKAGS (SEQ ID NO: 21).

In various embodiments, the fusion molecule comprises a antibody that specifically binds an antigen selected from the group consisting of CD70, CD127, CD30, CD40L/CD154, CD25, CD69, CD71, HLA-DR, CD38, CD97, CD134/OX40, CD137/4-1BB, MUC18/CD146, CD152/CTLA-4, CD195/FasL, CD212/IL-12R, LAG-3/CD223, TRAIL/CD253, DR6, CD278/ICOS, CD279/PD-1, and Kv1.3.

In various embodiments, the fusion molecule comprises a human IFN-β molecule, or mutant molecule thereof, and an anti-CD70 antibody.

In various embodiments, the fusion molecule comprises a human IFN-β molecule, or mutant molecule thereof, and an anti-CD127 antibody.

In various embodiments, the fusion molecule comprises a human IFN-β molecule, or mutant molecule thereof, and an anti-CD30 antibody.

In various embodiments, the fusion molecule comprises a human IFN-β molecule, or mutant molecule thereof, and an anti-CD40L/CD154 antibody.

In various embodiments, the fusion molecule comprises a human IFN-β molecule, or mutant molecule thereof, and an anti-CD25 antibody.

In various embodiments, the fusion molecule comprises a human IFN-β molecule, or mutant molecule thereof, and an anti-CD69 antibody.

In various embodiments, the fusion molecule comprises a human IFN-β molecule, or mutant molecule thereof, and an anti-CD71 antibody.

In various embodiments, the fusion molecule comprises a human IFN-β molecule, or mutant molecule thereof, and an anti-HLA-DR antibody.

In various embodiments, the fusion molecule comprises a human IFN-β molecule, or mutant molecule thereof, and an anti-CD38 antibody.

In various embodiments, the fusion molecule comprises a human IFN-β molecule, or mutant molecule thereof, and an anti-CD97 antibody.

In various embodiments, the fusion molecule comprises a human IFN-β molecule, or mutant molecule thereof, and an anti-CD134/OX40 antibody.

In various embodiments, the fusion molecule comprises a human IFN-β molecule, or mutant molecule thereof, and an anti-CD137/4-1BB antibody.

In various embodiments, the fusion molecule comprises a human IFN-β molecule, or mutant molecule thereof, and an anti-MUC18/CD146 antibody.

In various embodiments, the fusion molecule comprises a human IFN-β molecule, or mutant molecule thereof, and an anti-CD152/CTLA-4 antibody.

In various embodiments, the fusion molecule comprises a human IFN-β molecule, or mutant molecule thereof, and an anti-CD195/FasL antibody.

In various embodiments, the fusion molecule comprises a human IFN-β molecule, or mutant molecule thereof, and an anti-CD212/IL-12R antibody.

In various embodiments, the fusion molecule comprises a human IFN-β molecule, or mutant molecule thereof, and an anti-LAG-3/CD223 antibody.

In various embodiments, the fusion molecule comprises a human IFN-β molecule, or mutant molecule thereof, and an anti-TRAIL/CD253 antibody.

In various embodiments, the fusion molecule comprises a human IFN-β molecule, or mutant molecule thereof, and an anti-DR6 antibody.

In various embodiments, the fusion molecule comprises a human IFN-β molecule, or mutant molecule thereof, and an anti-CD278/ICOS antibody.

In various embodiments, the fusion molecule comprises a human IFN-β molecule, or mutant molecule thereof, and an anti-CD279/PD-1 antibody.

In various embodiments, the fusion molecule comprises a human IFN-β molecule, or mutant molecule thereof, and an anti-Kv1.3 antibody.

In various embodiments, the fusion molecule comprises a human IFN-α molecule, or mutant molecule thereof, and an anti-CD70 antibody.

In various embodiments, the fusion molecule comprises a human IFN-α molecule, or mutant molecule thereof, and an anti-CD127 antibody.

In various embodiments, the fusion molecule comprises a human IFN-α molecule, or mutant molecule thereof, and an anti-CD30 antibody.

In various embodiments, the fusion molecule comprises a human IFN-α molecule, or mutant molecule thereof, and an anti-CD40L/CD154 antibody.

In various embodiments, the fusion molecule comprises a human IFN-α molecule, or mutant molecule thereof, and an anti-CD25 antibody.

In various embodiments, the fusion molecule comprises a human IFN-α molecule, or mutant molecule thereof, and an anti-CD69 antibody.

In various embodiments, the fusion molecule comprises a human IFN-α molecule, or mutant molecule thereof, and an anti-CD71 antibody.

In various embodiments, the fusion molecule comprises a human IFN-α molecule, or mutant molecule thereof, and an anti-HLA-DR antibody.

In various embodiments, the fusion molecule comprises a human IFN-α molecule, or mutant molecule thereof, and an anti-CD38 antibody.

In various embodiments, the fusion molecule comprises a human IFN-α molecule, or mutant molecule thereof, and an anti-CD97 antibody.

In various embodiments, the fusion molecule comprises a human IFN-α molecule, or mutant molecule thereof, and an anti-CD134/OX40 antibody.

In various embodiments, the fusion molecule comprises a human IFN-α molecule, or mutant molecule thereof, and an anti-CD137/4-1BB antibody.

In various embodiments, the fusion molecule comprises a human IFN-α molecule, or mutant molecule thereof, and an anti-MUC18/CD146 antibody.

In various embodiments, the fusion molecule comprises a human IFN-α molecule, or mutant molecule thereof, and an anti-CD152/CTLA-4 antibody.

In various embodiments, the fusion molecule comprises a human IFN-α molecule, or mutant molecule thereof, and an anti-CD195/FasL antibody.

In various embodiments, the fusion molecule comprises a human IFN-α molecule, or mutant molecule thereof, and an anti-CD212/IL-12R antibody.

In various embodiments, the fusion molecule comprises a human IFN-α molecule, or mutant molecule thereof, and an anti-LAG-3/CD223 antibody.

In various embodiments, the fusion molecule comprises a human IFN-α molecule, or mutant molecule thereof, and an anti-TRAIL/CD253 antibody.

In various embodiments, the fusion molecule comprises a human IFN-α molecule, or mutant molecule thereof, and an anti-DR6 antibody.

In various embodiments, the fusion molecule comprises a human IFN-α molecule, or mutant molecule thereof, and an anti-CD278/ICOS antibody.

In various embodiments, the fusion molecule comprises a human IFN-α molecule, or mutant molecule thereof, and an anti-CD279/PD-1 antibody.

In various embodiments, the fusion molecule comprises a human IFN-α molecule, or mutant molecule thereof, and an anti-Kv1.3 antibody.

In various embodiments, the fusion molecule comprises an antibody selected from the group consisting of a fully human antibody, a humanized antibody, a chimeric antibody, a monoclonal antibody, a polyclonal antibody, a recombinant antibody, an antigen-binding antibody fragment, Fab, Fab', $Fab_2$, $Fab'_2$, IgG, IgM, IgA, IgE, scFv, dsFv, dAb, nanobodies, unibodies, and diabodies. In various embodiments, the antibody is a full length antibody. In various embodiments, the antibody is a humanized antibody.

Another aspect of the present invention relates to a pharmaceutical composition, and method of preparing said pharmaceutical composition, wherein said composition comprises a genetically engineered fusion molecule of the present invention as an active ingredient, in a pharmaceutically acceptable carrier or excipient. In various embodiments, the pharmaceutical composition is formulated for administration via a route selected from the group consisting of subcutaneous, intraperitoneal, intramuscular, intrasternal, intravenous, intraarterial, intrathecal, intraventricular, intraurethral, intracranial, and intrasynovial injection or infusions.

Another aspect of the present invention relates to a method for treatment, prophylaxis and/or prevention of an autoimmune disease. In various embodiments the autoimmune disease will be selected from the group consisting of systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis (RA), and scleroderma, comprising administering to a subject a pharmaceutical composition comprising a fusion molecule of the present invention.

Another aspect of the present invention relates to a method for impairing the function of an activated T cell, said method comprising contacting said activated T cell with a therapeutically effective amount of a pharmaceutical composition which comprises a genetically engineered fusion molecule of the present invention as an active ingredient.

Another aspect of the present invention relates to a method for inducing apoptosis and programmed cell death on an activated T cell, said method comprising contacting said activated T cell with a therapeutically effective amount of a pharmaceutical composition which comprises a genetically engineered fusion molecule of the present invention as an active ingredient.

Another aspect of the present invention relates to the use of a genetically engineered fusion molecule of the present invention for the preparation of a medicament for treatment, prophylaxis and/or prevention of an autoimmune disease in a patient in need thereof.

Other aspects of the present invention relate to nucleic acids that encode the genetically engineered fusion molecules of the present invention; vectors comprising nucleic acid molecules encoding fusion molecules of the invention, optionally, operably-linked to control sequences recognized by a host cell transformed with the vector; host cells comprising vectors comprising nucleic acid molecules encoding fusion molecules of the invention; a process for producing a fusion molecule of the invention comprising culturing host cells comprising vectors comprising nucleic acid molecules encoding fusion molecules of the invention so that the nucleic acid is expressed and, optionally, recovering the fusion molecule from the host cell culture medium.

BRIEF DESCRIPTION OF THE DRAWINGS

In FIG. 1, the ovals labeled as $V_L$, $V_H$, $C_L$, $C_{H1}$, $C_{H2}$ and $C_{H3}$ represent a full length antibody (Ab) as defined herein. The oval labeled C represents a cytokine, e.g., an IFN-β. A linker is represented by the squiggled line. As depicted in FIG. 1, C is attached to the Ab via a linker at the two $C_{H3}$ sites. In one alternative embodiment, C is attached to the Ab via a linker at the two $V_L$ sites. In yet another alternative embodiment, C will be attached to the Ab via a linker at the two $V_H$ sites. In yet another alternative, C will be attached to the Ab via a linker at an internal site rather than at the $C_{H3}$, $V_L$, or $V_H$ sites.

In FIG. 2, the ovals labeled as $V_L$, $V_H$, $C_L$, $C_H$, and $C_{H1}$ represent a $F(ab')_2$ as defined herein. The oval label C represents a cytokine. A linker is represented by the squiggled line. As depicted in FIG. 2, C is attached to the $F(ab')_2$ via a linker at the two $C_{H1}$ sites. In one alternative embodiment, C will be attached to the $F(ab')_2$ via a linker at the two $V_L$ sites rather than the $C_{H1}$ sites. In yet another alternative, C will be attached to the $F(ab')_2$ via a linker at the two $V_H$ sites rather than two $V_L$ or two $C_{H1}$ sites. In yet another alternative, C will be attached to the $F(ab')_2$ via a linker at an internal site rather than at the $C_{H1}$, $V_L$, or $V_H$ sites.

In FIG. 3, the ovals labeled as $V_L$, $V_H$, $C_L$, and $C_{H1}$ represent a Fab as defined herein. The oval label C represents a cytokine. A linker is represented by the squiggled line. As depicted in FIG. 3, C is attached to the Fab via a linker at the $C_{H1}$ site. In one alternative embodiment, C will be attached to the Fab via a linker at the $V_L$ site rather than the $C_{H1}$. In yet another alternative, C will be attached to the Fab via a linker at the $V_H$ site rather than the $V_L$ or $C_{H1}$ sites. In yet another alternative, C will be attached to the Fab via a linker at an internal site rather than at the $C_{H1}$, $V_L$, or $V_H$ sites.

SEQUENCE LISTINGS

Figure 1:
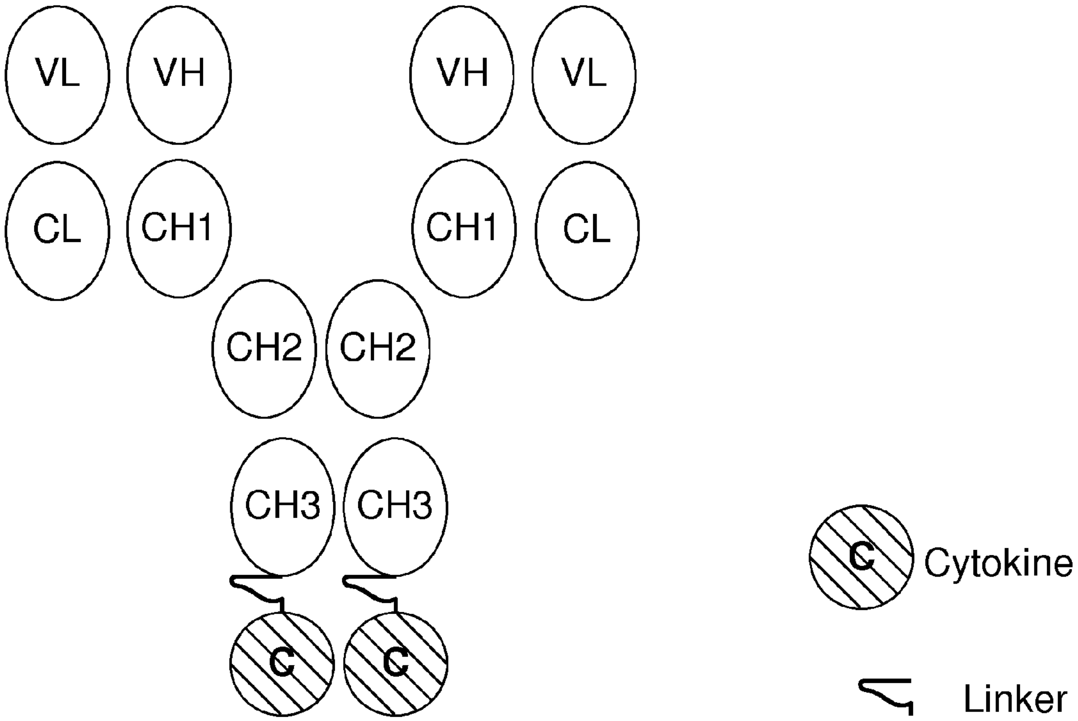
FIG. 1 depicts one proposed design for a genetically engineered fusion molecule of the present invention.

The amino acid sequences listed in the accompanying sequence listing are shown using standard three letter code for amino acids, as defined in 37 C.F.R. 1.822.

SEQ ID NO: 1 is the amino acid sequence of the heavy chain variable region of an anti-CD70 antibody. SEQ ID NO: 2 is the amino acid sequence encoding the light chain variable region of an anti-CD70 antibody.

SEQ ID NO: 3 is the amino acid sequence of the heavy chain variable region of an anti-CD30 antibody. SEQ ID NO: 4 is the amino acid sequence encoding the light chain variable region of an anti-CD30 antibody.

SEQ ID NO: 5 is the amino acid sequence of the heavy chain variable region of an anti-CD40L/CD154 antibody. SEQ ID NO: 6 is the amino acid sequence encoding the light chain variable region of an anti-CD40L/CD154 antibody.

SEQ ID NO: 7 is the amino acid sequence of the heavy chain variable region of an anti-CD25 antibody. SEQ ID NO: 8 is the amino acid sequence encoding the light chain variable region of an anti-CD25 antibody.

SEQ ID NO: 9 is the amino acid sequence of the heavy chain variable region of an anti-CD134/OX40 antibody. SEQ ID NO: 10 is the amino acid sequence encoding the light chain variable region of an anti-CD134/OX40 antibody.

SEQ ID NO: 11 is the amino acid sequence of the heavy chain variable region of an anti-CD137/4-1BB antibody. SEQ ID NO: 12 is the amino acid sequence encoding the light chain variable region of an anti-CD137/4-1BB antibody.

SEQ ID NO: 13 is the amino acid sequence of the heavy chain variable region of an anti-CD278/ICOS antibody. SEQ ID NO: 14 is the amino acid sequence encoding the light chain variable region of an anti-CD278/ICOS antibody.

SEQ ID NO: 15 is the amino acid sequence of the heavy chain variable region of an anti-CD279/PD-1 antibody. SEQ ID NO: 16 is the amino acid sequence encoding the light chain variable region of an anti-CD279/PD-1 antibody.

SEQ ID NO: 17 is the amino acid sequence of a human wildtype IFN-β-1a molecule.

SEQ ID NO: 18 is the amino acid sequence of a human wildtype IFN-β-1b molecule.

SEQ ID NO: 19 is the amino acid sequence of a human wildtype IFN-α2 molecule.

SEQ ID NO: 20 is the amino acid sequence of a peptide linker.

SEQ ID NO: 21 is the amino acid sequence of a peptide linker.

MODE(S) FOR CARRYING OUT THE INVENTION

The present invention provides novel genetically engineered fusion molecules comprising an interferon (IFN) molecule attached to an antibody (Ab) which targets a protein which is differentially expressed or up-regulated on activated T cells (as compared to resting T cells) for treating autoimmune diseases. One approach used by the present inventors to genetically engineer the fusion molecules of the present invention is as follows: 1) prepared an antibody, or mutant thereof, which binds to a targeted antigen determined to be differentially expressed or up-regulated on activated T cells as compared to resting cells; 2) prepared various IFN molecules (full length or truncated), or mutants thereof; 3) constructed several Ab-IFN fusion molecules wherein said antibody, or mutant thereof, is attached to said IFN molecule, or mutant thereof, via a peptide linker; 4) systematically tested the resulting Ab-IFN fusion molecules at varying doses in vitro to identify those fusion molecules with the best activity to impair functions of T cells or kill activated T cells which express the antigen to which the Ab portion of the fusion molecule binds; and 5) performed in vivo studies using the best Ab-IFN fusion molecules of step 4) to identify those fusion molecules with the best therapeutic efficacy. Therapeutic efficacy is defined as potency of the fusion molecule at killing activated T cells which express the antigen to which the Ab portion of the fusion molecule binds.

As a result of this engineering approach, the Ab-IFN fusion molecules of the present invention combine the specificity of the antibodies to the target antigen with the potent cytotoxic effects of the IFN molecule, thus sparing non-targeted cells, reducing the systemic toxicity of IFN, improving the on target effects and the activity of the antibody, and resulting in a local pro-apoptosis signal induced by the IFN. In other words, the Ab-IFN fusion molecules will have at least three major advantages as compared with non-fused IFN: 1) the fusion molecules have reduced IFN activity which addresses the adverse effects of non-fused IFN; 2) the potent cytotoxic effects (induced apoptosis and programmed cell death) of IFN is concentrated at the activated T cells by the fusion molecule (as compared with non-fused IFN); and 3) the IFN part of the fusion molecule does not have cytotoxic effects on healthy cells, including those cells which express the targeted antigen to which the antibody binds. The fusion molecules of the present invention thus provide for monoclonal antibody/IFN-based therapies having superior efficacy and safety profile for the treatment of autoimmune diseases.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of patients.

As used herein, an "antibody" refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

In a full-length antibody, each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$ (and in some instances, $C_{H4}$). Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: $FR_1$, $CDR_1$, $FR_2$, $CDR_2$, $FR_3$, $CDR_3$, $FR_4$. The extent of the framework region and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The CDRs are primarily responsible for binding to an epitope of an antigen. The CDRs of each chain are typically referred to as $CDR_1$, $CDR_2$, $CDR_3$, numbered sequentially starting from the N-terminus, and are also typically identified by the chain in which the particular CDR is located. Thus, a $V_H$ $CDR_3$ is located in the variable domain of the heavy chain of the antibody in which it is found, whereas a $V_L$ $CDR_1$ is the $CDR_1$ from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The Kabat definition is a standard for numbering the residues in an antibody and is typically used to identify CDR regions. The Kabat database is now maintained online and CDR sequences can be determined, for example, see IMGT/V-QUEST programme version: 3.2.18., Mar. 29, 2011, available on the internet and Brochet, X. et al., Nucl. Acids Res. 36, W503-508, 2008). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc. Natl. Acad. Sci. (U.S.A.), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a $C_{H2}$ domain and a $C_{H3}$ domain, and optionally comprises a $C_{H4}$ domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

Antibodies exist as intact immunoglobulins or as a number of well characterized fragments. Such fragments include Fab fragments, Fab' fragments, $Fab_2$, $F(ab)'_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), intrabodies, and epitope-binding fragments or antigen binding fragments of any of the above.

Papain digestion of antibodies produces two identical antigen-binding fragments, called "Fab" fragments, each with a single antigen-binding site. A "Fab fragment" comprises one light chain and the $C_{H1}$ and variable regions of one heavy chain. The heavy chain of a Fab molecule cannot form a disulfide bond with another heavy chain molecule.

A "Fab' fragment" comprises one light chain and a portion of one heavy chain that contains the $V_H$ domain and the $C_{H1}$ domain and also the region between the $C_{H1}$ and $C_{H2}$ domains, such that an interchain disulfide bond can be formed between the two heavy chains of two Fab' fragments to form an $F(ab')_2$ molecule.

Pepsin treatment of an antibody yields an $F(ab')_2$ fragment that has two antigen-combining sites and is still capable of cross-linking antigen. A "$F(ab')_2$ fragment" contains two light chains and two heavy chains containing a portion of the constant region between the $C_{H1}$ and $C_{H2}$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649, U.S. Pat. Nos. 4,946,778 and 5,260,203, the disclosures of which are incorporated by reference.

The terms "an antigen-binding fragment" and "antigen-binding protein" as used herein means any protein that binds a specified target antigen. In the instant application, the specified target antigen is cell surface CD70 protein or fragment thereof. "Antigen-binding fragment" includes but is not limited to antibodies and binding parts thereof, such as immunologically functional fragments. An exemplary antigen-binding fragment of an antibody is the heavy chain and/or light chain CDR(s), or the heavy and/or light chain variable region.

The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody, Fab', $F(ab')_2$, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

Diabodies are bivalent antibodies comprising two polypeptide chains, wherein each polypeptide chain comprises $V_H$ and $V_L$ regions joined by a linker that is too short to allow for pairing between two regions on the same chain, thus allowing each region to pair with a complementary region on another polypeptide chain (see, e.g., Holliger et al., 1993, Proc. Natl. Acad. Sci. (U.S.A.), 90:6444-48 (1993), and Poljak et al., Structure, 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

In certain embodiments, antibodies and antibody fragments used in the constructs of the present invention can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al., Proc. Natl. Acad. Sci. (U.S.A.), 78:5807, 1981), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method.

The term "chimeric antibody" as used herein refers to an antibody which has framework residues from one species, such as human, and CDRs (which generally confer antigen binding) from another species, such as a murine antibody that specifically binds targeted antigen.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular $CDR_3$. However, the term "human antibody", as used herein, is not intended to include antibodies in which CDR sequences derived from the germline of another mammalian species, such as a mouse, have been grafted onto human framework sequences.

The term "humanized antibody" as used herein refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions.

The term "recombinant human antibody", as used herein, is intended to include all human antibodies that are prepared, expressed, created or isolated by recombinant means, such as antibodies expressed using a recombinant expression vector transfected into a host cell; antibodies isolated from a recombinant, combinatorial human antibody library; antibodies isolated from an animal (e.g., a mouse) that is transgenic for human immunoglobulin genes; or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. All such recombinant means are well known to those of ordinary skill in the art.

The term "epitope" as used herein includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen.

An antigen binding protein, including an antibody, "specifically binds" to an antigen if it binds to the antigen with a high binding affinity as determined by a dissociation constant ($K_D$, or corresponding Kb, as defined below) value of at least $1\times10^{-6}$ M, or at least $1\times10^{-7}$ M, or at least $1\times10^{-8}$ M, or at least $1\times10^{-9}$ M, or at least $1\times10^{-10}$ M, or at least $1\times10^{-11}$ M. An antigen binding protein that specifically binds to the human antigen of interest may be able to bind to the same antigen of interest from other species as well, with the same or different affinities. The term "$K_D$" as used herein refers to the equilibrium dissociation constant of a particular antibody-antigen interaction.

The term "surface plasmon resonance" as used herein refers to an optical phenomenon that allows for the analysis of real-time biospecific interactions by detection of alterations in protein concentrations within a biosensor matrix, for example using the BIACORE system (Pharmacia Biosensor AB, Uppsala, Sweden and Piscataway, N.J.). For further descriptions, see Jonsson U. et al., Ann. Biol. Clin., 51:19-26, 1993; Jonsson U. et al., Biotechniques, 11:620-627, 1991; Jonsson B. et al., J. Mol. Recognit., 8:125-131, 1995; and Johnsson B. et al., Anal. Biochem., 198:268-277, 1991.

The terms "polypeptide", "peptide" and "protein" are used interchangeably herein to refer to a polymer of amino acid residues. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. (1991) Nature 354:105).

A "variant" of a polypeptide comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention. Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

The term "operably linked" used herein refers to sequences which include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "immunogenicity" as used herein refers to the ability of an antibody or antigen binding fragment to elicit an immune response (humoral or cellular) when administered to a recipient and includes, for example, the human anti-mouse antibody (HAMA) response. A HAMA response is initiated when T-cells from a subject make an immune response to the administered antibody. The T-cells then recruit B-cells to generate specific "anti-antibody" antibodies.

The term "immune cell" as used herein means any cell of hematopoietic lineage involved in regulating an immune response against an antigen (e.g., an autoantigen). In certain embodiments, an immune cell is a T lymphocyte, a B lymphocyte, or a dendritic cell.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

T cell Associated Antigens and Antibodies

The term "antigen" as used herein refers to a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term “antigen” includes all related antigenic epitopes. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least three, at least five, or at least eight to ten amino acids in a unique spatial conformation. Methods of determining spatial conformation of epitopes include, for example, x-ray crystallography and 2-dimensional nuclear magnetic resonance.

As relates to “targeted antigens”, virtually any antigen may be targeted by the molecules of the present invention, but the primary focus will be on those antigens which have been determined to be differentially expressed or up-regulated on activated T cells as compared to resting T cells. In various embodiments the targeted antigen is selected from the group consisting of CD70 (Grewal I, et al. Expert Opin Ther Targets, 12(3):341-51, 2008) (Tesselaar et al., J. Immunol., 170:33-40, 2003), CD127/IL-7Ra (Liu et al., J. Exp. Med. 203:1701, 2006), CD30 (Oflazoglu E, et al., Adv Exp Med Biol., 647:174-85, 2009), CD40L/CD154 (Grewal I, et al., Immunol Rev., 153:85-106, 1996), CD25 (Caruso A, et al., Cytometry, 27(1):71-6, 1997), CD69 (Caruso A, et al., Cytometry, 27(1):71-6, 1997), CD71 (Caruso A, et al., Cytometry, 27(1):71-6, 1997), HLA-DR(Caruso A, et al., Cytometry, 27(1):71-6, 1997), CD38 (Sandoval-Montes C and Santos-Argumedo L, J Leukoc Biol., 77(4):513-21, 2005), CD97 (Eichler W, et al., Tissue Antigens, 50(5):429-38, 1997), CD134/OX40 (Gadisseur A P, et al., Bone Marrow Transplant, 23(10):1013-7, 1999), CD137/4-1BB (Litjens N H, et al., Clin Exp Immunol. 2013 Jun. 10. doi: 10.1111/cei.12152. [Epub ahead of print]), MUC18/CD146, J Immunol. 1997 Mar. 1; 158(5):2107-15, 1997), CD152/CTLA-4 (Harper K, et al., J Immunol., 147(3):1037-44, 1991) CD195/FasL (Ju S T, et al, Nature, 373(6513):444-8, 1995), CD212/IL-12R (Desai B B, et al., J Immunol, 148 (10):3125-32, 1992), LAG-3/CD223 (Annunziato F, et al., FASEB J., 10(7):769-76, 1996), TRAIL/CD253 (Gras C, et al., J Immunol Methods., 387(1-2):147-56, 2013), DR6 (Zhao H, et al., J Exp Med., 194(10):1441-8, 2001), CD278/ICOS (Hutloff A, et al., Nature, 397(6716):263-6, 1999), CD279/PD-1 (Blank C, et al., Cancer Immunol Immunother., 56(5):739-45, 2007) and Kv1.3 (Beeton C, et al., Pro Natl Acad Sci USA.; 103(46):17414-9, 2006). The genetically engineered fusion molecules of the present invention may bind one antigen or multiple antigens.

Methods of generating novel antibodies that bind to antigens differentially expressed or up-regulated on activated T cells are known to those skilled in the art. For example, a method for generating a monoclonal antibody that binds specifically to a targeted antigen polypeptide may comprise administering to a mouse an amount of an immunogenic composition comprising the targeted antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the targeted antigen polypeptide. Once obtained, a hybridoma can be propagated in a cell culture, optionally in culture conditions where the hybridoma-derived cells produce the monoclonal antibody that binds specifically to targeted antigen polypeptide. The monoclonal antibody may be purified from the cell culture. A variety of different techniques are then available for testing an antigen/antibody interaction to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. (U.S.A.), 90: 2551-2555, 1993; Jakobovits et al., Nature, 362: 255-258, 1993; Lonberg et al., U.S. Pat. No. 5,545,806; and Surani et al., U.S. Pat. No. 5,545,807.

Antibodies can be engineered in numerous ways. They can be made as single-chain antibodies (including small modular immunopharmaceuticals or SMIPs™), Fab and $F(ab')_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., Science, 240:1041-1043, 1988; Liu et al., Proc. Natl. Acad. Sci. (U.S.A.), 84:3439-3443, 1987; Liu et al., J. Immunol., 139:3521-3526, 1987; Sun et al., Proc. Natl. Acad. Sci. (U.S.A.), 84:214-218, 1987; Nishimura et al., Canc. Res., 47:999-1005, 1987; Wood et al., Nature, 314:446-449, 1985; and Shaw et al., J. Natl Cancer Inst., 80:1553-1559, 1988).

Methods for humanizing antibodies have been described in the art. In some embodiments, a humanized antibody has one or more amino acid residues introduced from a source that is nonhuman, in addition to the nonhuman CDRs. Humanization can be essentially performed following the method of Winter and co-workers (Jones et al., Nature, 321:522-525, 1986; Riechmann et al., Nature, 332:323-327, 1988; Verhoeyen et al., Science, 239:1534-1536, 1988), by substituting hypervariable region sequences for the corresponding sequences of a human antibody. Accordingly, such “humanized” antibodies are chimeric antibodies (U.S. Pat. No. 4,816,567) wherein substantially less than an intact human variable region has been substituted by the corresponding sequence from a nonhuman species. In practice, humanized antibodies are typically human antibodies in which some hypervariable region residues and possibly some framework region residues are substituted by residues from analogous sites in rodent antibodies.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, the importance of particular framework amino acid residues is determined experimentally once a low-avidity humanized construct is obtained, by reversion of single residues to the mouse sequence and assaying antigen binding as described by Riechmann et al, 1988. Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

The choice of human variable regions, both light and heavy, to be used in making the humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296, 1993; Chothia et al., J. Mol. Biol., 196:901, 1987). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. (U.S.A.), 89:4285, 1992; Presta et al., J. Immunol., 151:2623, 1993).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an anti-CD70 antibody or antigen-binding fragment thereof comprises the steps of synthesizing a library of human antibodies on phage, screening the library with CD70 or an antibody-binding portion thereof, isolating phage that bind CD70, and obtaining the antibody from the phage. By way of another example, one method for preparing the library of antibodies for use in phage display techniques comprises the steps of immunizing a non-human animal comprising human immunoglobulin loci with CD70 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-CD70 antibodies of the invention may be obtained in this way.

Again, by way of example, recombinant human anti-CD70 antibodies of the invention can also be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology, 9:1370-1372 (1991); Hay et al., Hum. Antibod. Hybridomas, 3:81-85, 1992; Huse et al., Science, 246:1275-1281, 1989; McCafferty et al., Nature, 348:552-554, 1990; Griffiths et al., EMBO J., 12:725-734, 1993; Hawkins et al., J. Mol. Biol., 226:889-896, 1992; Clackson et al., Nature, 352:624-628, 1991; Gram et al., Proc. Natl. Acad. Sci. (U.S.A.), 89:3576-3580, 1992; Garrad et al., Bio/Technology, 9:1373-1377, 1991; Hoogenboom et al., Nuc. Acid Res., 19:4133-4137, 1991; and Barbas et al., Proc. Natl. Acad. Sci. (U.S.A.), 88:7978-7982, 1991), all incorporated herein by reference.

Human antibodies are also produced by immunizing a non-human, transgenic animal comprising within its genome some or all of human immunoglobulin heavy chain and light chain loci with a human IgE antigen, e.g., a XENOMOUSE™ animal (Abgenix, Inc./Amgen, Inc.—Fremont, Calif.). XENOMOUSE™ mice are engineered mouse strains that comprise large fragments of human immunoglobulin heavy chain and light chain loci and are deficient in mouse antibody production. See, e.g., Green et al., Nature Genetics, 7:13-21, 1994 and U.S. Pat. Nos. 5,916,771, 5,939,598, 5,985,615, 5,998,209, 6,075,181, 6,091,001, 6,114,598, 6,130,364, 6,162,963 and 6,150,584. XENOMOUSE™ mice produce an adult-like human repertoire of fully human antibodies and generate antigen-specific human antibodies. In some embodiments, the XENOMOUSE™ mice contain approximately 80% of the human antibody V gene repertoire through introduction of megabase sized, germline configuration fragments of the human heavy chain loci and kappa light chain loci in yeast artificial chromosome (YAC). In other embodiments, XENOMOUSE™ mice further contain approximately all of the human lambda light chain locus. See Mendez et al., Nature Genetics, 15:146-156, 1997; Green and Jakobovits, J. Exp. Med., 188:483-495, 1998; and WO 98/24893.

Antibodies that bind to antigens differentially expressed or up-regulated on activated T cells are known to those skilled in the art. For example, various anti-CD70 antibodies have been described in the art (see, e.g., U.S. Pat. No. 7,662,387 (Law et al) and references cited therein); various anti-CD30 antibodies have been described in the art (see, e.g., U.S. Pat. No. 8,257,706 (McDonagh et al) and references cited therein); various anti-CD40L/CD154 antibodies have been described in the art (see, e.g., U.S. Pat. No. 6,440,418 (Black et al) and references cited therein); various anti-CD25 antibodies have been described in the art (see, e.g., U.S. Pat. No. 7,438,907 (Shuurmanetal et al) and references cited therein); various anti-CD134/OX40 antibodies have been described in the art (see, e.g., U.S. Patent Application No. 20100196359 (Kato et al) and references cited therein); various anti-CD137/4-1BB antibodies have been described in the art (see, e.g., U.S. Pat. No. 7,288,638 (Jure-Kunkel et al) and references cited therein); various anti-CD278/ICOS antibodies have been described in the art (see, e.g., U.S. Pat. No. 6,803,039 (Tsuji et al) and references cited therein); various anti-CD279/PD-1 antibodies have been described in the art (see, e.g., U.S. Pat. No. 7,488,802 (Collins et al) and references cited therein); various anti-CD127 antibodies have been described in the art (see, e.g., U.S. Pat. Public. No. 20100040616 (Leung et al) and references cited therein); various anti-CD127 antibodies have been described in the art (see, e.g., U.S. Pat. Public. No. 20100040616 (Leung et al) and references cited therein); various anti-CD38 antibodies have been described in the art (see, e.g., U.S. Pat. Public. No. 20110262454 (Park et al) and references cited therein); various anti-CD69 antibodies have been described in the art (see, e.g., U.S. Pat. No. 8,440,195 (Nakayama et al) and references cited therein); various anti-CD71 antibodies have been described in the art (see, e.g., U.S. Pat. No. 8,409,573 (Boumsell et al) and references cited therein); various anti-HLA-DR antibodies have been described in the art (see, e.g., U.S. Pat. No. 6,894,149 (Tso et al) and references cited therein); various anti-MUC18/CD146 antibodies have been described in the art (see, e.g., U.S. Pat. Public. No. 20060246077 (Bar-Eli et al) and references cited therein); various anti-CD152/CTLA-4 antibodies have been described in the art (see, e.g., U.S. Pat. Public. No. 20130136749 (Korman et al) and references cited therein); various anti-CD195/FasL antibodies have been described in the art (see, e.g., U.S. Pat. Public. No. 20050106140 (Lancaster, Joanne) and references cited therein); various anti-LAG-3/CD223 antibodies have been described in the art (see, e.g., U.S. Pat. Public. No. 20110150892 (Thudium et al) and references cited therein); various anti-TRAIL/CD253 antibodies have been described in the art (see, e.g., U.S. Pat. No. 6,521,228 (Wiley et al) and references cited therein); various anti-DR6 antibodies have been described in the art (see, e.g., U.S. Pat. Public. No. 20100203044 (Nikolaev et al) and references cited therein);

various anti-Kv1.3 antibodies have been described in the art (see, e.g., Yang et al, J. Lipid Res., 54:(1), 34-43, 2013); various anti-CD212/IL-12R antibodies have been described in the art (see, e.g., U.S. Pat. No. 6,046,012 (Chizzonite et al) and references cited therein).

In various embodiments of the present invention the antibody is an anti-CD70 antibody which comprises the heavy chain variable region sequence as set forth in SEQ ID NO: 1:

(SEQ ID NO: 1)
MAWVWTLLFLMAAAQSAGAQIQLVQSGPEVKKPGETVKISCKASGYTF
TNYGMNWVKQAPGKGLKWMGWINTYTGEPTYADAFKGRFAFSLETSAS
TAYLQINNLKNGDTATYFCARDYGDYGMDYWGQGTSVTVSS and the light chain variable region sequence as set forth in SEQ ID NO: 2:

(SEQ ID NO: 2)
METDTLLLWVLLLWVPGSTGDIVLTQSPASLAVSLGQRATISCRASKSV
STSGYSFMHWYQQKPGQPPKLLIYLASNLESGVPARFSGSGSGTDFTLN
IHPVEEEDAATYYCQHSREVPWTFGGGTKLEIKR

In various embodiments the antibody is an anti-CD30 antibody which comprises the heavy chain variable region sequence as set forth in SEQ ID NO: 3:

(SEQ ID NO: 3)
QVQLVQSGAEVKKPGASVKVSCKASGYTFTDYYITWVRQAPGQGLEWMG
WIYPGSGNTKYNGKFKGRVTMTRDTSISTAYMELSRLRSDDTAVYYCAN
YGNYWFAYWGQGTLVTVSS and the light chain variable region sequence as set forth in SEQ ID NO: 4:

(SEQ ID NO: 4)
DIVMTQSPDSLAVSLGERATINCKASQSVDFDGDSYMNWYQQKPGQPPK
LLIYAASNLESGVPDRFSGSGSGTDFTLTISSLQAEDVAVYYCQQSNED
PWTFGQGTKVEIK

In various embodiments the antibody is an anti-CD40L/CD154 antibody which comprises the heavy chain variable region sequence as set forth in SEQ ID NO: 5:

(SEQ ID NO: 5)
EVQLQESGPGLVKPSETLSLTCTVSGDSITNGFWIWIRKPPGNKLEY
MGYISYSGSTYYNPSLKSRISISRDTSKNQFSLKLSSVTAADTGVYY
CACRSYGRTPYYFDFWGQGTTLTVSS and the light chain variable region sequence as set forth in SEQ ID NO: 6:

(SEQ ID NO: 6)
DIVMTQSPSFLSASVGDRVTITCKASQNVITAVAWYQQKPGKSPKLL
IYSASNRYTGVPDRFSGSGSGTDFTLTISSLQPEDFADYFCQQYNSY
PYTFGGGTKLEIK

In various embodiments the antibody is an anti-CD25 antibody which comprises the heavy chain variable region sequence as set forth in SEQ ID NO: 7:

(SEQ ID NO: 7)
QVQLVQSGAEVKKPGSSVKVSCKASGGTFSRYAINWVRQAPGQGLEW

MGRIIPILDIADYAQKFQDRVTITADKSTNTAYMELSSLRSEDTAVY

YCARKDWFDPWGQGTLVTVSSASTKGPSVFPLA and the light chain variable region sequence as set forth in SEQ ID NO: 8:

(SEQ ID NO: 8)
ENVLTQSPGTLSLSPGERATLSCRASQSGSSSYLAWYQQKPGQAPRL

LIYGASSRATGIPDRFSGSGSGTDFTLTISRLEPEDFAVYYCQQYGS

SPITFGQGTRLEIKRTVAAPSVFIFP

In various embodiments the antibody is an anti-CD134/OX40 antibody which comprises the heavy chain variable region sequence as set forth in SEQ ID NO: 9:

(SEQ ID NO: 9)
QLVESGGGLVQPGGSLRLSCAASGFTFSSYSMNWVRQAPGKGLEWVS

YISSSSSTIYYADSVKGRFTISRDNAKNSLYLQMNSLRDEDTAVYYC

ARGVYHNGWSFFDYWGQGTLLTVSS and the light chain variable region sequence as set forth in SEQ ID NO: 10:

(SEQ ID NO: 10)
RCDIQMTQSPSSLSASVGNRVTITCRASQDISSWLAWYQQKPEKAPK

SLIYAASSLQSGVPSRFSGSGSGTDFTLTISSLQPEDFATYYCQQYN

SYPLTFGQGTRLEIKR

In various embodiments the antibody is an anti-CD137/4-1BB antibody which comprises
the heavy chain variable region sequence as set forth in SEQ ID NO: 11:

(SEQ ID NO: 11)
QVQLQQWGAGLLKPSETLSLTCAVYGGSFSGYYWSWIRQSPEKGLEW

IGEINHGGYVTYNPSLESRVTISVDTSKNQFSLKLSSVTAADTAVYY

CARDYGPGNYDWYFDLWGRGTLVTVSS and the light chain variable region sequence as set forth in SEQ ID NO: 12:

(SEQ ID NO: 12)
EIVLTQSPATLSLSPGERATLSCRASQSVSSYLAWYQQKPGQAPRLL

IYDASNRATGIPARFSGSGSGTDFTLTISSLEPEDFAVYYCQQRSNW

PPALTFGGGTKVEIK

In various embodiments the antibody is an anti-CD278/ICOS antibody which comprises the heavy chain variable region sequence as set forth in SEQ ID NO: 13:

(SEQ ID NO: 13)
QVQLVQSGAEVKKPGASVKVSCKASGYTFTGYYMHWVRQAPGQGLEW

MGWINPHSGGTNYAQKFQGRVTMTRDTSISTAYMELSRLRSDDTAVY

YCAR and the light chain variable region sequence as set forth in SEQ ID NO: 14:

(SEQ ID NO: 14)
DIQMTQSPSSVSAVSGDRVTITCRASQGISRLLAWYQQKPGKAPKLL

IYVASSLQSGVPSRFSGSGSGTDFTLTISSLQPGDFATYYCQQANSF

In various embodiments the antibody is an anti-CD279/PD-1 antibody which comprises the heavy chain variable region sequence as set forth in SEQ ID NO: 15:

(SEQ ID NO: 15)
QVQLVQSGAEVKKPGASVKVSCKASGYRFTSYGISWVRQAPGQGLEW

MGWISAYNGNTNYAQKLQGRVTMTTDTSTNTAYMGLRSLRSDDTAVY

YCARDADYSSGSGYWGQGTLVTVSS and the light chain variable region sequence as set forth in SEQ ID NO: 16:

(SEQ ID NO: 16)
SYELTQPPSVSVSPGQTARITCSGDALPKQYAYWYQQKPGQAPVMVI

YKDTGRPSGIPERFSGSSSGTKVTLTISGVQAEDEADYYCQSADNSI

TYRVFGGGTKVTVL

Interferon and Interferon Mutants

In certain embodiments of the present invention, either the N- or C-terminus of an antibody heavy or light chain will be genetically constructed with one of the several contemplated interferons or interferon mutants. The term "interferon" refers to a full-length interferon or to an interferon fragment (truncated interferon) or an interferon mutant (truncated interferon and interferon mutant collectively referred to herein as 'modified interferon'), that substantially retains the biological activity of the full length wild-type interferon (e.g., retains at least 50%). Interferons include type I interferons (e.g., interferon-alpha and interferon-beta) as well as type II interferons (e.g., interferon-gamma). Typically the interferon fragment is one that possesses the endogenous activity of the native interferon, preferably at a level of at least 80%, more preferably at least 90% or 95%, most preferably at least 98%, 99%, 100%, or a level greater than the wild-type interferon. The interferon can be from essentially any mammalian species. In certain various embodiments, the interferon is from a species selected from the group consisting of human, equine, bovine, rodent, porcine, lagomorph, feline, canine, murine, caprine, ovine, a non-human primate, and the like. In various embodiments the modified interferon comprises one or more amino acid substitutions, insertions, and/or deletions.

In various embodiments of the present invention, the interferon mutant comprises one or more amino acid substitutions, insertions, and/or deletions. Means of identifying such modified interferon molecules are routine to those of skill in the art. In one illustrative approach, a library of truncated and/or mutated IFN-α is produced and screened for IFN-α activity. Methods of producing libraries of polypeptide variants are well known to those of skill in the art. Thus, for example error-prone PCR can be used to create a library of mutant and/or truncated IFN-α (see, e.g., U.S. Pat. No. 6,365,408). The resultant library members can then be screened according to standard methods know to those of skill in the art. Thus, for example, IFN-α activity can be assayed by measuring antiviral activity against a particular test virus. Kits for assaying for IFN-α activity are commercially available (see, e.g., ILITE™ alphabeta kit by Neutekbio, Ireland).

The use of chemically modified interferons is also contemplated. For example, in certain embodiments, the interferon is chemically modified to increase serum half-life. Thus, for example, (2-sulfo-9-fluorenylmethoxycarbonyl)$_7$-interferon-α2 undergoes time-dependent spontaneous hydrolysis, generating active interferon (Shechter et al., Proc. Natl. Acad. Sci., USA, 98(3): 1212-1217, 2001). Other modifications, include for example, N-terminal modifications in including, but not limited to the addition of PEG, protecting groups, and the like (see, e.g., U.S. Pat. No. 5,824,784).

In various embodiments use of a wildtype IFN-β-1a provided below as SEQ ID NO: 17:

(SEQ ID NO: 17)

MSYNLLGFLQRSSNFQCQKLLWQLNGRLEYCLKDRMNFDIPEEIKQL

QQFQKEDAALTIYEMLQNIFAIFRQDSSSTGWNETIVENLLANVYHQ

INHLKTVLEEKLEKEDFTRGKLMSSLHLKRYYGRILHYLKAKEYSHC

AWTIVRVEILRNFYFINRLTGYLRN is contemplated.

In various embodiments use of a wildtype IFN-β-1b provided below as SEQ ID NO: 18:

(SEQ ID NO: 18)

MSYNLLGFLQRSSNFQSQKLLWQLNGRLEYCLKDRMNFDIPEEIKQL

QQFQKEDAALTIYEMLQNIFAIFRQDSSSTGWNETIVENLLANVYHQ

INHLKTVLEEKLEKEDFTRGKLMSSLHLKRYYGRILHYLKAKEYSHC

AWTIVRVEILRNFYFINRLTGYLRN is contemplated.

In various embodiments use of a mutated IFN-β is contemplated. A mutated IFN-β comprising a serine substituted for the naturally occurring cysteine at amino acid 17 of IFN-β-1a has also been demonstrated to show efficacy (Hawkins et al., Cancer Res., 45:5914-5920, 1985). Certain C-terminally truncated IFN-β-1a's have been shown to have increased activity (see, e.g., U.S. Patent Publication 2009/0025106 A1). Accordingly, in certain embodiments the interferons used in the constructs described herein include the C-terminally truncated IFN-β described as IFN-Δ1, IFN-Δ2, IFN-Δ3, IFN-Δ4, IFN-Δ5, IFN-Δ6, IFN-Δ7, IFN-Δ8, IFN-Δ9, IFN-Δ10 in US 2009/0025106 A1. In certain embodiments the interferon is IFN-Δ7, IFN-Δ8, IFN-Δ9 (SEQ ID NOs: 57, 59, and 61 in US 2009/0025106 A1).

In various embodiments use of a mutated IFN-α is contemplated. Single point mutations contemplated for use herein include, but are not limited to, a series of mostly single point mutants (see Table 1 below) that are considered important to the binding affinity of IFN-α to IFN-αR1 based on published information on NMR structure with the assumption that a single point mutation may change the binding affinity but will not completely knock off the activity of IFN-α, therefore still retaining the antiproliferative properties albeit at much higher concentrations. This will potentially improve the therapeutic index of the fusion molecules comprising an antibody fused to the interferon-alpha mutants. As described herein and as depicted in Table 1, a single mutation will be identified by the particular amino acid substitution at a specific amino acid position within the full length wild type interferon sequence. For example, a mutation comprising a tyrosine substituted for the full length wild type histidine at amino acid 57 is identified as H57Y. The wild type IFN-α2 amino acid sequence from which the mutants described in Table 1 are derived is provided below as SEQ ID NO: 19:

(SEQ ID NO: 19)

CDLPQTHSLGSRRTLMLLAQMRRISLFSCLKDRHDFGFPQEEFGNQF

QKAETIPVLHEMIQQIFNLFSTKDSSAAWDETLLDKFYTELYQQLND

LEACVIQGVGVTETPLMKEDSILAVRKYFQRITLYLKEKKYSPCAWE

VVRADIVIRSFSLSTNLQESLRSKE

TABLE 1

List of proposed Ab-IFN-α Mutant Fusion Molecules.

| | IFN-α sequence mutations | Selection Criteria |
|---|---|---|
| M1 | H57Y, E58N, Q61S | Phage display optimization of selected IFN-α residues to increase IFN-α-IFN-αR1 binding affinity of Site 1 |
| M2 | H57S, E58S, Q61S | Decrease the IFN-α-IFN-αR1 binding affinity at Site 1 based on triple mutations predicted to result in a loss of binding contacts between IFNα and IFN-αR1 |
| M3 | H57A | Decrease the IFN-α-IFN-αR1 binding affinity at Site 1 similar to M2 but only single point |
| M4 | E58A | Decrease the IFN-α-IFN-αR1 binding affinity at Site 1 similar to M2 but only single point |
| M5 | Q61A | Decrease the IFN-α-IFN-αR1 binding affinity at Site 1 similar to M2 but only single point |
| M6 | R149A | Decrease the IFN-α-IFN-αR1 binding affinity at Site 2 based on loss of binding contacts |
| M7 | R162A | Decrease the IFN-α-IFN-αR1 binding affinity at Site 2 based on loss of binding contacts |
| M8 | R149A, R162A | Decrease the IFN-α-IFN-αR1 binding affinity at Site 2 based on loss of binding contacts |
| M9 | L30A | Decrease the IFN-α-IFN-αR1 binding affinity at Site 2 based on loss of binding contacts |
| M10 | D35E | Alter the IFN-α-IFN-αR1 binding at Site 2 based on minimal change in structure |
| M11 | E165D | Alter the IFN-α-IFN-αR1 binding at Site 2 based on minimal change in structure |
| M12 | L26A | Alter the IFN-α-IFN-αR1 binding at Site 2 based on minimal change in structure |

TABLE 1-continued

List of proposed Ab-IFN-α Mutant Fusion Molecules.

| | IFN-α sequence mutations | Selection Criteria |
|---|---|---|
| M13 | F27A | Alter the IFN-α-IFN-αR1 binding at Site 2 based on minimal change in structure |
| M14 | L153A | Alter the IFN-α-IFN-αR1 binding at Site 2 based on minimal change in structure |
| M15 | A145V | Alter the IFN-α-IFN-αR1 binding at Site 2 based on minimal change in structure |

Fusion Molecules

Figure 2:
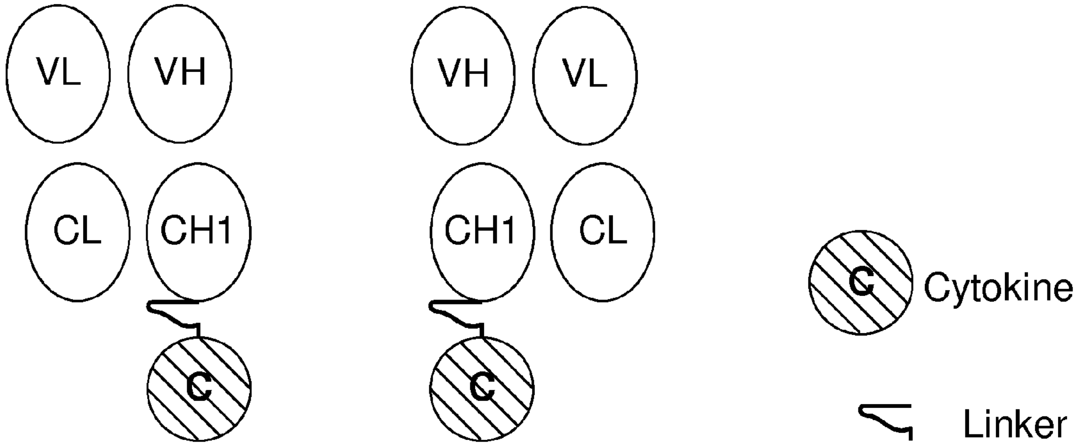
FIG. 2 depicts another proposed design for a genetically engineered fusion molecule of the present invention.
Figure 3:
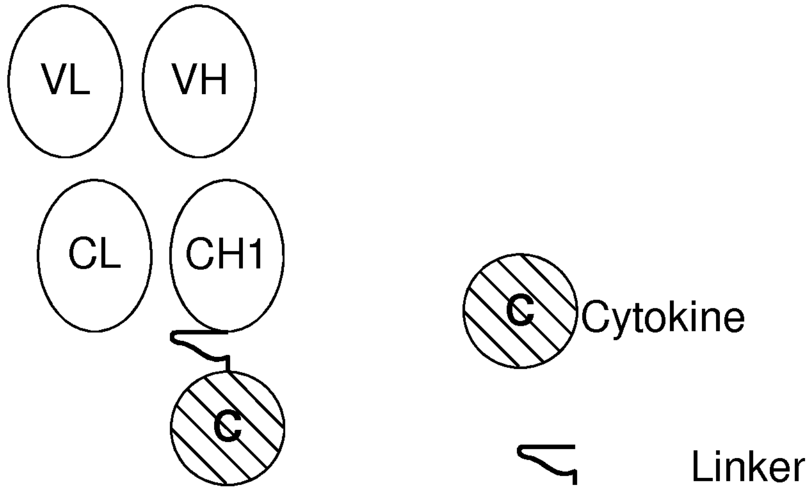
FIG. 3 depicts another proposed design for a genetically engineered fusion molecule of the present invention.

The present invention further relates to genetically engineered fusion molecules comprising at least one antibody, or antigen-binding fragment thereof, attached to at least one interferon, or interferon mutant molecule, formed through genetic fusion or by chemical coupling. Generally speaking, the antibody and interferon molecule of the genetically engineered fusion molecules of the present invention can be joined together in any order. Thus, for example, the interferon molecule can be joined to either the amino or carboxy terminal of the antibody; or conversely, the interferon molecule can be joined to an internal location of the antibody, so long as the attachment does not interfere with binding of the antibody to the target antigen. Alternatively, the antibody can be joined to either the amino or carboxy terminal of the interferon molecule; or joined to an internal region of the interferon molecule. In various embodiments, the fusion molecule is a recombinantly expressed fusion molecule and will comprise an interferon molecule attached to the antibody via a peptide linker as described herein and as depicted in, e.g., any of the FIGS. 1-3.

In certain embodiments, the antibody and interferon molecule are linked directly to each other and synthesized using recombinant DNA methodology. By "linked" we mean that the first and second sequences are associated such that the second sequence is able to be transported by the first sequence to a target cell, i.e., fusion molecules in which the antibody is linked to a IFN-α molecule via their polypeptide backbones through genetic expression of a DNA molecule encoding these proteins, directly synthesized proteins, and coupled proteins in which pre-formed sequences are associated by a cross-linking agent.

In certain embodiments, the two molecules can be separated by a peptide spacer ("linker") consisting of one or more amino acids. Generally the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity.

The term "linker" is thus used herein to denote polypeptides comprising two or more amino acid residues joined by peptide bonds and are used to link the antibody and interferon molecules of the present invention. In various embodiments, the linker is capable of forming covalent bonds to both the antibody and to the interferon. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the interferon through their side groups (e.g., through a disulfide linkage to cysteine). In certain preferred embodiments, the linkers are joined to the alpha carbon amino and/or carboxyl groups of the terminal amino acids of the antibody and/or the interferon. Such linker polypeptides are well known in the art (see e.g., Holliger, P., et al., Proc. Natl. Acad. Sci. (U.S.A.), 90:6444, 1993; Poljak, R. J., et al., Structure, 2:1121, 1994). Linker length contemplated for use can vary from about 5 to 200 amino acids. In certain embodiments, the linker may be a proteolysis-resistant linker (see, e.g., Morrison et al., U.S. Pat. No. 8,258,263). In certain embodiments, the proteolysis-resistant linker is SGGGGS (SEQ ID NO: 20) or AEAAAKEAAAKAGS (SEQ ID NO: 21).

In certain alternative embodiments, the antibody is chemically conjugated to the interferon molecule. Means of chemically conjugating molecules are well known to those of skill. The procedure for conjugating two molecules varies according to the chemical structure of the agent. Polypeptides typically contain variety of functional groups; e.g., carboxylic acid (COOH) or free amine ($—NH_2$) groups, that are available for reaction with a suitable functional group on the other peptide, or on a linker to join the molecules thereto. Alternatively, the antibody and/or the cytokine mutant can be derivatized to expose or attach additional reactive functional groups. The derivatization can involve attachment of any of a number of linker molecules such as those available from Pierce Chemical Company, Rockford Ill.

In various embodiments, the fusion molecules of the present invention will comprise the antibody, peptide linker, and interferon molecule combinations recited in Table 2.

TABLE 2

Examples of Ab-IFN Fusion Molecules

| Antibody | Peptide Linker | Interferons |
|---|---|---|
| Anti-CD70 | SEQ ID NO: 20 or SEQ ID NO: 21 | wtIFN-β (SEQ ID NO: 17 or 18)<br>wtIFN-α (SEQ ID NO: 19) |
| Anti-CD30 | SEQ ID NO: 20 or SEQ ID NO: 21 | wtIFN-β (SEQ ID NO: 17 or 18)<br>wtIFN-α (SEQ ID NO: 19) |
| Anti-CD40L/CD154 | SEQ ID NO: 20 or SEQ ID NO: 21 | wtIFN-β (SEQ ID NO: 17 or 18)<br>wtIFN-α (SEQ ID NO: 19) |
| Anti-CD25 | SEQ ID NO: 20 or SEQ ID NO: 21 | wtIFN-β (SEQ ID NO: 17 or 18)<br>wtIFN-α (SEQ ID NO: 19) |
| Anti-CD134/OX40 | SEQ ID NO: 20 or SEQ ID NO: 21 | wtIFN-β (SEQ ID NO: 17 or 18)<br>wtIFN-α (SEQ ID NO: 19) |

TABLE 2-continued

Examples of Ab-IFN Fusion Molecules

| Antibody | Peptide Linker | Interferons |
|---|---|---|
| Anti-CD137/4-1BB | SEQ ID NO: 20 or SEQ ID NO: 21 | wtIFN-β (SEQ ID NO: 17 or 18)<br>wtIFN-α (SEQ ID NO: 19) |
| Anti-CD278/ICOS | SEQ ID NO: 20 or SEQ ID NO: 21 | wtIFN-β (SEQ ID NO: 17 or 18)<br>wtIFN-α (SEQ ID NO: 19) |
| Anti-CD279/PD-1 | SEQ ID NO: 20 or SEQ ID NO: 21 | wtIFN-β (SEQ ID NO: 17 or 18)<br>wtIFN-α (SEQ ID NO: 19) |
| Anti-CDKv1.3 | SEQ ID NO: 20 or SEQ ID NO: 21 | wtIFN-β (SEQ ID NO: 17 or 18)<br>wtIFN-α (SEQ ID NO: 19) |
| Anti-CD127 | SEQ ID NO: 20 or SEQ ID NO: 21 | wtIFN-β (SEQ ID NO: 17 or 18)<br>wtIFN-α (SEQ ID NO: 19) |
| Anti-CD69 | SEQ ID NO: 20 or SEQ ID NO: 21 | wtIFN-β (SEQ ID NO: 17 or 18)<br>wtIFN-α (SEQ ID NO: 19) |
| Anti-CD71 | SEQ ID NO: 20 or SEQ ID NO: 21 | wtIFN-β (SEQ ID NO: 17 or 18)<br>wtIFN-α (SEQ ID NO: 19) |
| Anti-HLA-DR | SEQ ID NO: 20 or SEQ ID NO: 21 | wtIFN-β (SEQ ID NO: 17 or 18)<br>wtIFN-α (SEQ ID NO: 19) |
| Anti-CD38 | SEQ ID NO: 20 or SEQ ID NO: 21 | wtIFN-β (SEQ ID NO: 17 or 18)<br>wtIFN-α (SEQ ID NO: 19) |
| Anti-CD97 | SEQ ID NO: 20 or SEQ ID NO: 21 | wtIFN-β (SEQ ID NO: 17 or 18)<br>wtIFN-α (SEQ ID NO: 19) |
| Anti-MUC18/CD146 | SEQ ID NO: 20 or SEQ ID NO: 21 | wtIFN-β (SEQ ID NO: 17 or 18)<br>wtIFN-α (SEQ ID NO: 19) |
| Anti-CD152/CTLA-4 | SEQ ID NO: 20 or SEQ ID NO: 21 | wtIFN-β (SEQ ID NO: 17 or 18)<br>wtIFN-α (SEQ ID NO: 19) |
| Anti-CD195/FasL | SEQ ID NO: 20 or SEQ ID NO: 21 | wtIFN-β (SEQ ID NO: 17 or 18)<br>wtIFN-α (SEQ ID NO: 19) |
| Anti-CD212/IL-12R | SEQ ID NO: 20 or SEQ ID NO: 21 | wtIFN-β (SEQ ID NO: 17 or 18)<br>wtIFN-α (SEQ ID NO: 19) |
| Anti-LAG-3/CD223 | SEQ ID NO: 20 or SEQ ID NO: 21 | wtIFN-β (SEQ ID NO: 17 or 18)<br>wtIFN-α (SEQ ID NO: 19) |
| Anti-TRAIL/CD253 | SEQ ID NO: 20 or SEQ ID NO: 21 | wtIFN-β (SEQ ID NO: 17 or 18)<br>wtIFN-α (SEQ ID NO: 19) |
| Anti-DR6 | SEQ ID NO: 20 or SEQ ID NO: 21 | wtIFN-β (SEQ ID NO: 17 or 18)<br>wtIFN-α (SEQ ID NO: 19) |

Nucleic acid Molecules and Fusion Molecule Expression

The present application further provides nucleic acid molecules comprising nucleotide sequences encoding the fusion molecules described herein. Because of the degeneracy of the genetic code, a variety of nucleic acid sequences encode each fusion molecule amino acid sequence. The application further provides nucleic acid molecules that hybridize under stringent or lower stringency hybridization conditions, e.g., as defined herein, to nucleic acid molecules that encode a fusion molecule. Stringent hybridization conditions include, but are not limited to, hybridization to filter-bound DNA in 6×SSC at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The nucleic acid molecules may be obtained, and the nucleotide sequence of the nucleic acid molecules determined by, any method known in the art. For example, if the nucleotide sequence of the fusion molecule is known, a nucleic acid molecule encoding the fusion molecule may be assembled from chemically synthesized oligonucleotides (e.g., as described in Kutmeier et al., BioTechniques 17:242, 1994), which, briefly, involves the synthesis of overlapping oligonucleotides containing portions of the sequence encoding the antibody, annealing and ligating of those oligonucleotides, and then amplification of the ligated oligonucleotides by PCR. In one embodiment, the codons that are used comprise those that are typical for human or mouse (see, e.g., Nakamura, Y., Nucleic Acids Res. 28: 292, 2000).

A nucleic acid molecule encoding a fusion molecule may also be generated from nucleic acid from a suitable source. For example, if a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

In one embodiment of the present invention, nucleic acid sequences encoding the appropriate antibody framework are optionally cloned and ligated into appropriate vectors (e.g., expression vectors for, e.g., prokaryotic or eukaryotic organisms). Additionally, nucleic acid sequences encoding the appropriate interferon molecule are optionally cloned into the same vector in the appropriate orientation and location so that expression from the vector produces an antibody-interferon molecule fusion molecule. Some optional embodiments also require post-expression modification, e.g., assembly of antibody subunits, etc. The techniques and art for the above (and similar) manipulations are well known to those skilled in the art. Pertinent instructions are found in, e.g., Sambrook et al., Molecular Cloning—A Laboratory Manual (2nd Ed.), Vols. 1-3, Cold Spring Harbor Laboratory, Cold Spring Harbor, N.Y., 1989 and Current Protocols in Molecular Biology, F. M. Ausubel et al., eds., Current Protocols, a joint venture between Greene Publishing Associates, Inc. and John Wiley & Sons, Inc. (supplemented through 1999).

The present invention is also directed to host cells that express the fusion molecules of the invention. Host cells suitable for replicating and for supporting recombinant expression of fusion protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as *E. coli*; various eukaryotic cells, such as Chinese hamster ovary cells (CHO), NSO, 293; HEK Yeast; insect cells; hybridomas; human cell lines; and transgenic animals and transgenic plants, and the like. Standard technologies are known in the art to express foreign genes in these systems. The recombinant protein gene is typically operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

To express an antibody-IFN fusion molecule recombinantly, a host cell is transformed, transduced, infected or the like with one or more recombinant expression vectors carrying DNA fragments encoding the immunoglobulin light and/or heavy chains of the antibody and attached interferon such that the light and/or heavy chains are expressed in the host cell. The heavy chain and the light chain may be expressed independently from different promoters to which they are operably-linked in one vector or, alternatively, the heavy chain and the light chain may be expressed independently from different promoters to which they are operably-linked in two vectors one expressing the heavy chain and one expressing the light chain. Optionally, the heavy chain and light chain may be expressed in different host cells.

Additionally, the recombinant expression vector can encode a signal peptide that facilitates secretion of the antibody light and/or heavy chain from a host cell. The antibody light and/or heavy chain gene can be cloned into the vector such that the signal peptide is operably-linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR can be converted to a full-length heavy chain gene by operably-linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g., IgG1, IgG2, IgG3 and IgG4) or subclass constant region and any allotypic variant thereof as described in Kabat (supra).

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

Additionally, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NSO) for selection/amplification.

For expression of the light and/or heavy chains with attached interferon, the expression vector(s) encoding the heavy and/or light chains is introduced into a host cell by standard techniques e.g. electroporation, calcium phosphate precipitation, DEAE-dextran transfection, transduction, infection and the like. Although it is theoretically possible to express the antibodies of the invention in either prokaryotic or eukaryotic host cells, eukaryotic cells and most specifically mammalian host cells, are more typical because such cells are more likely to assemble and secrete a properly folded and immunologically active antibody. Mammalian host cells for expressing the recombinant antibodies of the invention include Chinese Hamster Ovary (CHO cells) [including dhfr minus CHO cells, as described in Urlaub and Chasin, Proc. Natl. Acad. Sci. USA 77:4216-20, 1980, used with a DHFR selectable marker, e.g. as described in Kaufman and Sharp, J. Mol. Biol. 159:601-21, 1982], NSO myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxyapatite chromatography, gel electrophoresis, and the like. Standard procedures for purification of therapeutic antibodies are described, for example, by Feng L1, Joe X. Zhou, Xiaoming Yang, Tim Tressel, and Brian Lee in an article entitled "Current Therapeutic Antibody Production and Process Optimization" (BioProcessing Journal, September/October 2005), for example. Additionally, standard techniques for removing viruses from recombinantly expressed antibody preparations are also known in the art (see, for example, Gerd Kern and Mani Krishnan, "Viral Removal by Filtration: Points to Consider" (Biopharm International, October 2006)). The effectiveness of filtration to remove viruses from preparations of therapeutic antibodies is known to be at least in part dependent on the concentration of protein and/or the antibody in the solution to be filtered. The purification process for antibodies of the present invention may include a step of filtering to remove viruses from the mainstream of one or more chromatography operations. Preferably, prior to filtering through a pharmaceutical grade nanofilter to remove viruses, a chromatography mainstream containing an antibody of the present invention is diluted or concentrated to give total protein and/or total antibody concentration of about 1 g/L to about 3 g/L. Even more preferably, the nanofilter is a DV20 nanofilter (e.g., Pall Corporation; East Hills, N.Y.). Substantially pure immunoglobulins of at least about 90%, about 92%, about 94% or about 96% homogeneity are preferred, and about 98 to about 99% or more homogeneity most preferred, for pharmaceutical uses. Once purified, partially or to homogeneity as desired, the sterile antibodies may then be used therapeutically, as directed herein.

In view of the aforementioned discussion, the present invention is further directed to a fusion molecule obtainable by a process comprising the steps of culturing a host cell including, but not limited to a mammalian, plant, bacterial, transgenic animal, or transgenic plant cell which has been transformed by a nucleic acid molecule or a vector comprising nucleic acid molecules encoding antibodies of the invention so that the nucleic acid is expressed and, optionally, recovering the antibody from the host cell culture medium.

Pharmaceutical Compositions

In one aspect, the present invention provides a pharmaceutical composition comprising a fusion molecule as described above. The pharmaceutical compositions, methods and uses of the invention thus also encompass embodiments of combinations (co-administration) with other active agents, as detailed below.

Generally, the fusion molecules of the invention are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the fusion molecules of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Various embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the fusion molecule in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The fusion molecules of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurized container, pump, spray, atomiser (preferably an atomiser using electrohydrodynamics to produce a fine mist), or nebulizer, with or without the use of a suitable propellant, or as nasal drops.

The pressurized container, pump, spray, atomizer, or nebulizer generally contains a solution or suspension of an antibody of the invention comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the compound of the invention, a suitable powder base and a performance modifier.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The fusion molecules of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

As used herein, the terms "co-administration", "co-administered" and "in combination with", referring to the fusion molecules of the invention and one or more other therapeutic agents, is intended to mean, and does refer to and include the following: simultaneous administration of such combination of fusion molecules of the invention and therapeutic agent(s) to a patient in need of treatment, when such components are formulated together into a single dosage form which releases said components at substantially the same time to said patient; substantially simultaneous administration of such combination of fusion molecules of the invention and therapeutic agent(s) to a patient in need of treatment, when such components are formulated apart from each other into separate dosage forms which are taken at substantially the same time by said patient, whereupon said components are released at substantially the same time to said patient; sequential administration of such combination of fusion molecules of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of fusion molecules of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

"Therapeutically effective amount" refers to that amount of the therapeutic agent being administered which will relieve to some extent one or more of the symptoms of the disorder being treated. A therapeutically effective amount can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition.

Dosage regimens may be adjusted to provide the optimum desired response. For example, a single bolus may be administered, several divided doses may be administered over time or the dose may be proportionally reduced or increased as indicated by the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

An exemplary, non-limiting range for a therapeutically or prophylactically effective amount of an antibody portion of the invention is 0.025 to 50 mg/kg, more preferably 0.1 to 50 mg/kg, more preferably 0.1-25, 0.1 to 10 or 0.1 to 3 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

Kits

In certain embodiments, this invention provides for kits for the treatment of a autoimmune disease. Kits typically comprise a container containing a fusion molecule of the present invention. The fusion molecule can be present in a pharmacologically acceptable excipient.

In addition the kits can optionally include instructional materials disclosing means of use of the fusion molecule to treat an autoimmune disease. The instructional materials may also, optionally, teach preferred dosages, counter-indications, and the like.

The kits can also include additional components to facilitate the particular application for which the kit is designed. Thus, for example, and additionally comprise means for disinfecting a wound, for reducing pain, for attachment of a dressing, and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Therapeutic Uses

Another aspect of the present invention relates to methods for treatment, prophylaxis and/or prevention of an autoimmune disease, comprising administering to said patient a therapeutically effective amount (either as monotherapy or in a combination therapy regimen) of a fusion molecule described herein, in pharmaceutically acceptable carrier, wherein such administration induces apoptosis and programmed cell death or impairment of function of an activated T cell to which the fusion molecule has contacted.

An autoimmune disease, as pertains to the present invention, is a disease or disorder arising from and directed against an individual's own tissues or a co-segregate or manifestation thereof or resulting condition therefrom. Examples of autoimmune diseases or disorders include, but are not limited to: arthritis, including rheumatoid arthritis, acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, juvenile-onset rheumatoid arthritis, osteoarthritis, arthritis chronica progrediente, arthritis deformans, polyarthritis chronica primaria, reactive arthritis, and ankylosing spondylitis; inflammatory hyperproliferative skin diseases; psoriasis, such as plaque psoriasis, gutatte psoriasis, pustular psoriasis, and psoriasis of the nails; atopy, including atopic diseases such as hay fever and Job's syndrome; dermatitis, including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis; x-linked hyper IgM syndrome; allergic intraocular inflammatory diseases; urticaria, such as chronic allergic urticaria, chronic idiopathic urticaria, and chronic autoimmune urticaria; myositis; polymyositis/dermatomyositis; juvenile dermatomyositis; toxic epidermal necrolysis; scleroderma, including systemic scleroderma; sclerosis, such as systemic sclerosis, multiple sclerosis (MS), spino-optical MS, primary progressive MS (PPMS), relapsing remitting MS (RRMS), progressive systemic sclerosis, atherosclerosis, arteriosclerosis, sclerosis disseminata, and ataxic sclerosis; neuromyelitis optica (NMO); inflammatory bowel disease (IBD), including Crohn's disease, autoimmune-mediated gastrointestinal diseases, colitis, ulcerative colitis, colitis ulcerosa, microscopic colitis, collagenous colitis, colitis polyposa, necrotizing enterocolitis, transmural colitis, and autoimmune inflammatory bowel disease; bowel inflammation; pyoderma gangrenosum; erythema nodosum; primary sclerosing cholangitis; respiratory distress syndrome, including adult or acute respiratory distress syndrome (ARDS); meningitis; inflammation of all or part of the uvea; iritis; choroiditis; an autoimmune hematological disorder; rheumatoid spondylitis; rheumatoid synovitis; hereditary angioedema; cranial nerve damage, as in meningitis; herpes gestationis; pemphigoid gestationis; pruritis scroti; autoimmune premature ovarian failure; sudden hearing loss due to an autoimmune condition; IgE-mediated diseases, such as anaphylaxis and allergic and atopic rhinitis; encephalitis, such as Rasmussen's encephalitis and limbic and/or brainstem encephalitis; uveitis, such as anterior uveitis, acute anterior uveitis, granulomatous uveitis, nongranulomatous uveitis, phacoantigenic uveitis, posterior uveitis, or autoimmune uveitis; glomerulonephritis (GN) with and without nephrotic syndrome, such as chronic or acute glomerulonephritis, primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN; proliferative nephritis; autoimmune polyglandular endocrine failure; balanitis, including balanitis circumscripta plasmacellularis; balanoposthitis; erythema annulare centrifugum; erythema dyschromicum perstans; eythema multiform; granuloma annulare; lichen nitidus; lichen sclerosus et atrophicus; lichen simplex chronicus; lichen spinulosus; lichen planus; lamellar ichthyosis; epidermolytic hyperkeratosis; premalignant keratosis; pyoderma gangrenosum; allergic conditions and responses; allergic reaction; eczema, including allergic or atopic eczema, asteatotic eczema, dyshidrotic eczema, and vesicular palmoplantar eczema; asthma, such as asthma bronchiale, bronchial asthma, and auto-immune asthma; conditions involving infiltration of T cells and chronic inflammatory responses; immune reactions against foreign antigens such as fetal A-B-O blood groups during pregnancy; chronic pulmonary inflammatory disease; autoimmune myocarditis; leukocyte adhesion deficiency; lupus, including lupus nephritis, lupus cerebritis, pediatric lupus, non-renal lupus, extra-renal lupus, discoid lupus and discoid lupus erythematosus, alopecia lupus, systemic lupus erythematosus (SLE), cutaneous SLE, subacute cutaneous SLE, neonatal lupus syndrome (NLE), and lupus erythematosus disseminatus; juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, and diabetic large-artery disorder; immune responses associated with acute and delayed hypersensitivity mediated by cytokines and T-lymphocytes; tuberculosis; sarcoidosis; granulomatosis, including lymphomatoid granulomatosis; Wegener's granulomatosis; agranulocytosis; vasculitides, including vasculitis, large-vessel vasculitis, polymyalgia rheumatica and giant-cell (Takayasu's) arteritis, medium-vessel vasculitis, Kawasaki's disease, polyarteritis nodosa/periarteritis nodosa, microscopic polyarteritis, immunovasculitis, CNS vasculitis, cutaneous vasculitis, hypersensitivity vasculitis, necrotizing vasculitis, systemic necrotizing vasculitis, ANCA-associated vasculitis, Churg-Strauss vasculitis or syndrome (CSS), and ANCA-associated small-vessel vasculitis; temporal arteritis; aplastic anemia; autoimmune aplastic anemia; Coombs positive anemia; Diamond Blackfan anemia; hemolytic anemia or immune hemolytic anemia, including autoimmune hemolytic anemia (AIHA), pernicious anemia (anemia perniciosa); Addison's disease; pure red cell anemia or aplasia (PRCA); Factor VIII deficiency; hemophilia A; autoimmune neutropenia; pancytopenia; leukopenia; diseases involving leukocyte diapedesis; CNS inflammatory disorders; multiple organ injury syndrome, such as those secondary to septicemia, trauma or hemorrhage; antigen-antibody complex-mediated diseases; anti-glomerular basement membrane disease; anti-phospholipid antibody syndrome; allergic neuritis; Behcet's disease/syndrome; Castleman's syndrome; Goodpasture's syndrome; Reynaud's syndrome; Sjogren's syndrome; Stevens-Johnson syndrome; pemphigoid, such as pemphigoid bullous and skin pemphigoid, pemphigus, pemphigus vulgaris, pemphigus foliaceus, pemphigus mucus-membrane pemphigoid, and pemphigus erythematosus; autoimmune polyendocrinopathies; Reiter's disease or syndrome; thermal injury; preeclampsia; an immune complex disorder, such as immune complex nephritis, and antibody-mediated nephritis; polyneuropathies; chronic neuropathy, such as IgM polyneuropathies and IgM-mediated neuropathy; thrombocytopenia (as developed by myocardial infarction patients, for example), including thrombotic thrombocytopenic purpura (TTP), post-transfusion purpura (PTP), heparin-induced thrombocytopenia, autoimmune or immune-mediated thrombocytopenia, idiopathic thrombocytopenic purpura (ITP), and chronic or acute ITP; scleritis, such as idiopathic cerato-scleritis, and episcleritis; autoimmune disease of the testis and ovary including, autoimmune orchitis and oophoritis; primary hypothyroidism; hypoparathyroidism; autoimmune endocrine diseases, including thyroiditis, autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes, autoimmune polyglandular syndromes, and polyglandular endocrinopathy syndromes; paraneoplastic syndromes, including neurologic paraneoplastic syndromes; Lambert-Eaton myasthenic syndrome or Eaton-Lambert syndrome; stiff-man or stiff-person syndrome; encephalomyelitis, such as allergic encephalomyelitis, encephalomyelitis allergica, and experimental allergic encephalomyelitis (EAE); myasthenia gravis, such as thymoma-associated myasthenia gravis; cerebellar degeneration; neuromyotonia; opsoclonus or opsoclonus myoclonus syndrome (OMS); sensory neuropathy; multifocal motor neuropathy; Sheehan's syndrome; hepatitis, including autoimmune hepatitis, chronic hepatitis, lupoid hepatitis, giant-cell hepatitis, chronic active hepatitis, and autoimmune chronic active hepatitis; lymphoid interstitial pneumonitis (LIP); bronchiolitis obliterans (non-transplant) vs NSIP; Guillain-Barre syndrome; Berger's disease (IgA nephropathy); idiopathic IgA nephropathy; linear IgA dermatosis; acute febrile neutrophilic dermatosis; subcorneal pustular dermatosis; transient acantholytic dermatosis; cirrhosis, such as primary biliary cirrhosis and pneumonocirrhosis; autoimmune enteropathy syndrome; Celiac or Coeliac disease; celiac sprue (gluten enteropathy); refractory sprue; idiopathic sprue; cryoglobulinemia; amylotrophic lateral sclerosis (ALS; Lou Gehrig's disease); coronary artery disease; autoimmune ear disease, such as autoimmune inner ear disease (AIED); autoimmune hearing loss; polychondritis, such as refractory or relapsed or relapsing polychondritis; pulmonary alveolar proteinosis; Cogan's syndrome/nonsyphilitic interstitial keratitis; Bell's palsy; Sweet's disease/syndrome; rosacea autoimmune; zoster-associated pain; amyloidosis; a non-cancerous lymphocytosis; a primary lymphocytosis, including monoclonal B cell lymphocytosis (e.g., benign monoclonal gammopathy and monoclonal gammopathy of undetermined significance, MGUS); peripheral neuropathy; channelopathies, such as epilepsy, migraine, arrhythmia, muscular disorders, deafness, blindness, periodic paralysis, and channelopathies of the CNS; autism; inflammatory myopathy; focal or segmental or focal segmental glomerulosclerosis (FSGS); endocrine opthalmopathy; uveoretinitis; chorioretinitis; autoimmune hepatological disorder; fibromyalgia; multiple endocrine failure; Schmidt's syndrome; adrenalitis; gastric atrophy; presenile dementia; demyelinating diseases, such as autoimmune demyelinating diseases and chronic inflammatory demyelinating polyneuropathy; Dressler's syndrome; alopecia areata; alopecia totalis; CREST syndrome (calcinosis, Raynaud's phenomenon, esophageal dysmotility, sclerodactyly, and telangiectasia); male and female autoimmune infertility (e.g., due to anti-spermatozoan antibodies); mixed connective tissue disease; Chagas' disease; rheumatic fever; recurrent abortion; farmer's lung; erythema multiforme; post-cardiotomy syndrome; Cushing's syndrome; bird-fancier's lung; allergic granulomatous angiitis; benign lymphocytic angiitis; Alport's syndrome; alveolitis, such as allergic alveolitis and fibrosing alveolitis; interstitial lung disease; transfusion reaction; leprosy; malaria; Samter's syndrome; Caplan's syndrome; endocarditis; endomyocardial fibrosis; diffuse interstitial pulmonary fibrosis; interstitial lung fibrosis; pulmonary fibrosis; idiopathic pulmonary fibrosis; cystic fibrosis; endophthalmitis; erythema elevatum et diutinum; erythroblastosis fetalis; eosinophilic faciitis; Shulman's syndrome; Felty's syndrome; flariasis; cyclitis, such as chronic cyclitis, heterochronic cyclitis, iridocyclitis (acute or chronic), or Fuch's cyclitis; Henoch-Schonlein purpura; sepsis; endotoxemia; pancreatitis; thyroxicosis; Evan's syndrome; autoimmune gonadal failure; Sydenham's chorea; post-streptococcal nephritis; thromboangitis ubiterans; thyrotoxicosis; tabes dorsalis; chorioiditis; giant-cell polymyalgia; chronic hypersensitivity pneumonitis; keratoconjunctivitis sicca; epidemic keratoconjunctivitis; idiopathic nephritic syndrome; minimal change nephropathy; benign familial and ischemia-reperfusion injury; transplant organ reperfusion; retinal autoimmunity; joint inflammation; bronchitis; chronic obstructive airway/pulmonary disease; silicosis; aphthae; aphthous stomatitis; arteriosclerotic disorders; aspermiogenese; autoimmune hemolysis; Boeck's disease; cryoglobulinemia; Dupuytren's contracture; endophthalmia phacoanaphylactica; enteritis allergica; erythema nodo sum leprosum; idiopathic facial paralysis; febris rheumatica; Hamman-Rich's disease; sensoneural hearing loss; haemoglobinuria paroxysmatica; hypogonadism; ileitis regionalis; leucopenia; mononucleosis infectiosa; traverse myelitis; primary idiopathic myxedema; nephrosis; ophthalmia symphatica; orchitis granulomatosa; pancreatitis; polyradiculitis acuta; pyoderma gangrenosum; Quervain's thyreoiditis; acquired spenic atrophy; non-malignant thymoma; vitiligo; toxic-shock syndrome; food poisoning; conditions involving infiltration of T cells; leukocyte-adhesion deficiency; immune responses associated with acute and delayed hypersensitivity mediated by cytokines and T-lymphocytes; diseases involving leukocyte diapedesis; multiple organ injury syndrome; antigen-antibody complex-mediated diseases; antiglomerular basement membrane disease; allergic neuritis; autoimmune polyendocrinopathies; oophoritis; primary myxedema; autoimmune atrophic gastritis; sympathetic ophthalmia; rheumatic diseases; mixed connective tissue disease; nephrotic syndrome; insulitis; polyendocrine failure; autoimmune polyglandular syndrome type I; adult-onset idiopathic hypoparathyroidism (AOIH); cardiomyopathy such as dilated cardiomyopathy; epidermolisis bullosa acquisita (EBA); hemochromatosis; myocarditis; nephrotic syndrome; primary sclerosing cholangitis; purulent or non-purulent sinusitis; acute or chronic sinusitis; ethmoid, frontal, maxillary, or sphenoid sinusitis; an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils; anaphylaxis; seronegative spondyloarthritides; polyendocrine autoimmune disease; sclerosing cholangitis; chronic mucocutaneous candidiasis; Bruton's syndrome; transient hypogammaglobulinemia of infancy; Wiskott-Aldrich syndrome; ataxia telangiectasia syndrome; angiectasis; autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization; allergic hypersensitivity disorders; glomerulonephritides; reperfusion injury; ischemic reperfusion disorder; reperfusion injury of myocardial or other tissues; lymphomatous tracheobronchitis; inflammatory dermatoses; dermatoses with acute inflammatory components; multiple organ failure; bullous diseases; renal cortical necrosis; acute purulent meningitis or other central nervous system inflammatory disorders; ocular and orbital inflammatory disorders; granulocyte transfusion-associated syndromes; cytokine-induced toxicity; narcolepsy; acute serious inflammation; chronic intractable inflammation; pyelitis; endarterial hyperplasia; peptic ulcer; valvulitis; and endometriosis.

In various embodiments the autoimmune disease is selected from the group consisting of systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis (RA), and scleroderma.

The following examples are provided to describe the invention in further detail.

Example 1

This example describes the preparation of genetically engineered fusion molecules comprising an interferon attached to an antibody which specifically binds an antigen which is differentially expressed or up-regulated on activated T cells, and wherein said interferon is attached to said antibody via proteolysis resistant linker. The molecules were initially constructed as depicted in FIG. 1, with the interferon molecule attached via a linker to the heavy chain of the antibody. The molecule in this example were prepared using methods and techniques well known and understood by one of ordinary skill in the art.

The preparation of the genetically engineered molecules of the present invention can be generally described as follows: the heavy chain of the antibody was recombinantly engineered with an IFN-β or IFN-α, or mutants thereof, at the carboxy-terminus using a proteolysis resistant linker, e.g., SEQ ID NO: 20 and SEQ ID NO: 21. After verifying that the fusion protein vector has the correct nucleotide sequence, it was transfected, along with the light chain vector into NSO cells. Transfectants were screened by ELISA for the production of the complete fusion molecule. The clone giving the highest signal was expanded and following sub-cloning was grown in roller bottles. Conditioned medium was collected, concentrated, and the protein of interest purified using a single Protein A affinity chromatography step or appropriate alternative chromatography methods. The final product was formulated in a desired buffer and at a desired concentration (the protein concentration is confirmed by UV absorption). The purity of the final product was determined by SDS-PAGE both under reducing and non-reducing conditions. Western blot analysis was used to confirm the expected size of the molecule.

Example 2

This example describes the evaluation and testing of the various Ab-IFN fusion molecules prepared as described in Example 1 at varying doses in various in vitro functional assays to identify Ab-IFN fusion molecules with the best activity to impair functions of T cells prepared from blood obtained from healthy volunteers and T cell lines previously described in the art (e.g., those described in the various references cited herein related to the target antigens and associated antibodies). Activity of the Ab-IFN fusion molecules will also be assessed for killing of activated T cells which express the antigen to which the Ab portion of the fusion molecule binds.

The fusion molecules demonstrating the best activity in the in vitro assays will then be tested in vivo to identify those fusion molecules with the best therapeutic efficacy. The in vivo activity of Ab-IFN fusion molecules will be evaluated in SCID-huPBMC mice immunized with tetanus toxoid. Effects of treatment with Ab-IFN fusion molecules on anti-TT antibody titers compared to untreated mice or to those that received non-binding control Ig. In addition, ability of treatment with Ab-IFN fusion molecules in elimination/killing of activated human T cell will be suited by previously described methods in the art (e.g., those described in the various references cited herein related to the targeted antigens and associated antibodies. Therapeutic efficacy is defined as potency of the fusion molecule at killing activated T cells which express the antigen to which the Ab portion of the fusion molecule binds and significant reduction in the anti-TT antibody titers compared to untreated mice or to those that received non-binding control Ig.

A. Evaluation of the Ability of the Fusion Molecules to Bind the IFN-αR Complex

Various methods previously described in the art can be used to determine the best methodology for assessing the binding of the fusion molecules to the IFN-αR complex. Such methods include ALEXA FLUOR® 555 (Invitrogen), QDOT® 565 (Invitrogen), or primary/secondary Ab FACS methodology (Invitrogen). Cells lines used include cell lines known to be very sensitive to the inhibitory effect of IFN-α or IFN-β on cell proliferation and where targeted antigen expression is very high, and cell lines known to be very sensitive to the inhibitory effect of IFN-α or IFN-β on cell proliferation but where targeted antigen expression is very low.

B. Evaluation of the Ability of the Fusion Molecules to Bind Cells Expressing the Targeted Antigen.

To determine the fusion molecule binding to the targeted antigen, targeted antigen expressing cells ($1\times10^6$) are incubated with the corresponding Ab-IFN fusion molecules or the control reagents. The binding of the fusion molecules is confirmed and then compared to binding of naked Ab. Cells are reacted with biotinylated rat anti-human IgG (BD Biosciences), followed by PE-labeled streptavidin (BD Biosciences) and then analyzed by flow cytometry using a FACScan (Becton Dickinson) and analyzed using FlowJo software (TreeStar Inc).

C. Evaluation of the IFN Bioactivity of the Fusion Molecules

To assess the anti-viral activity of the Ab-IFN fusion molecules, WISH cells (transformed human cell line of epitheloid morphology) are seeded at $2\times10^5$ cells/ml and treated with two-fold serial dilutions of the fusion molecules or recombinant human interferon alpha-2a, or recombinant human interferon beta-1a (or 1b) for 24 hrs. Cells are then infected with VSV (vesicular stomatitis virus) at a concentration of 4000 pfu/100 μl. After 72 hrs, cells are stained with 0.1% crystal violet. Protection against viral infection is determined either by quantitating the cells surviving the infection by staining with 0.1% crystal violet and determining the amount of dye in each well using a spot densitometer of by counting the number of plaques.

D. In Vitro Anti-Proliferative Effects

To assess the ability of the fusions molecules to inhibit/kill activated T cells, freshly isolated human T cells, or target expressing T cell lines are incubated with various concentrations of IFN-α, IFN-β, naked antibody or fusion molecule for 72 hrs and growth inhibition assessed using the CellTiter 96 AQueous cell proliferation assay. Alternatively, targeted antigen expressing cells are incubated with various concentrations of IFN-α, IFN-β, naked antibody or fusion molecule for 72 hrs and then stained with Annexin V and propidium iodide (PI) and analyzed by FLOW cytometry.

E. Determination of Apoptosis

Purified human CD4 T cells will be stimulated with anti-CD3 antibody and anti-CD28 antibody. Various amounts of the Ab-IFN fusion molecule, or control antibody will be added to cultures. After 3-4 days of culture, apoptosis of T cells will be determined by washing the cells with ice-cold PBS, and the Annexin V/propidium iodide (PI) assay will be conducted using the Vybrant Apoptosis Assay Kit #2 following procedures suggested by the manufacturer (Molecular Probes). The percentage of apoptotic cells is calculated as the sum of the percentages of early apoptotic cells and late apoptotic cells.

F. Determination of Cytokine Secretion by Activated T Cells

Purified human CD4 T cells will be stimulated with anti-CD3 antibody and anti-CD28 antibody. Various amounts of the Ab-IFN fusion molecule, or control antibody will be added to cultures. After 3-4 days of culture, supernatants will be assayed for presence of cytokines such as IL-2, IL-4, IFN-γ, IL-17, etc., using commercially available ELISA kits and following manufacturers recommended protocols (e.g., kits obtained from BD Biosciences).

G. In Vivo Efficacy

To determine the in vivo efficacy of the Ab-IFN fusion molecule, peripheral blood leucocytes from individuals whose T cells proliferated against dominant tetanus toxid (TT) peptides will be injected intraperitoneally (i.p.) into mice with severe combined immunodeficiency (SCID) that had been depleted of murine natural killer cells (hu-PBL-SCID mice). Ab-IFN fusion molecule or PBS will be injected i.p. before a further injection of PBL and immunization with TT. The concentration of human IgG and anti-TT in murine plasma will be followed for 10 weeks (Jackson D J, et al., Clin Exp Immunol., August, 137(2):245-52, 2004).

Example 3

In this example, a fusion molecule comprising: 1) an anti-CD70 antibody and wildtype IFN-β-1a molecule; 2) an anti-CD70 antibody and wildtype IFN-β-1b molecule; and 3) an anti-CD70 antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD70 antibody comprised the heavy chain variable region amino acid sequence and light chain variable region amino acid sequence depicted in SEQ ID NO: 1 and SEQ ID NO: 2, respectfully.

The various fusion molecules were then tested in the various in vitro functional assays described in Example 2 to identify anti-CD70Ab-IFN fusion molecules possessing the best activity to impair functions of activated T cells. The best performers were then assessed in vivo for killing activated T cells which express the antigen to which the Ab portion of the fusion molecule binds.

Example 4

In this example, a fusion molecule comprising: 1) an anti-CD30 antibody and wildtype IFN-β-1a molecule; 2) an anti-CD30 antibody and wildtype IFN-β-1b molecule; and 3) an anti-CD30 antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD30 antibody comprised the heavy chain variable region amino acid sequence and light chain variable region amino acid sequence depicted in SEQ ID NO: 3 and SEQ ID NO: 4, respectfully.

The various fusion molecules were then tested in the various in vitro functional assays described in Example 2 to identify anti-CD30Ab-IFN fusion molecules possessing the best activity to impair functions of activated T cells. The best performers were then assessed in vivo for killing activated T cells which express the antigen to which the Ab portion of the fusion molecule binds.

Example 5

In this example, a fusion molecule comprising: 1) an anti-CD40L/CD154 antibody and wildtype IFN-β-1a molecule; 2) an anti-CD40L/CD154 antibody and wildtype IFN-β-1b molecule; and 3) an anti-CD40L/CD154 antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD40L/CD154 antibody comprised the heavy chain variable region amino acid sequence and light chain variable region amino acid sequence depicted in SEQ ID NO: 5 and SEQ ID NO: 6, respectfully.

The various fusion molecules were then tested in the various in vitro functional assays described in Example 2 to identify anti-CD40L/CD154Ab-IFN fusion molecules possessing the best activity to impair functions of activated T cells. The best performers were then assessed in vivo for killing activated T cells which express the antigen to which the Ab portion of the fusion molecule binds.

Example 6

In this example, a fusion molecule comprising: 1) an anti-CD25 antibody and wildtype IFN-β-1a molecule; 2) an anti-CD25 antibody and wildtype IFN-β-1b molecule; and 3) an anti-CD25 antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD25 antibody comprised the heavy chain variable region amino acid sequence and light chain variable region amino acid sequence depicted in SEQ ID NO: 7 and SEQ ID NO: 8, respectfully.

The various fusion molecules were then tested in the various in vitro functional assays described in Example 2 to identify anti-CD25Ab-IFN fusion molecules possessing the best activity to impair functions of activated T cells. The best performers were then assessed in vivo for killing activated T cells which express the antigen to which the Ab portion of the fusion molecule binds.

Example 7

In this example, a fusion molecule comprising: 1) an anti-CD134/OX40 antibody and wildtype IFN-β-1a molecule; 2) an anti-CD134/OX40 antibody and wildtype molecule; and 3) an anti-CD134/OX40 antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD134/OX40 antibody comprised the heavy chain variable region amino acid sequence and light chain variable region amino acid sequence depicted in SEQ ID NO: 9 and SEQ ID NO: 10, respectfully.

The various fusion molecules were then tested in the various in vitro functional assays described in Example 2 to identify anti-CD134/OX40 Ab-IFN fusion molecules possessing the best activity to impair functions of activated T cells. The best performers were then assessed in vivo for killing activated T cells which express the antigen to which the Ab portion of the fusion molecule binds.

Example 8

In this example, a fusion molecule comprising: 1) an anti-CD137/4-IBB antibody and wildtype IFN-β-1a molecule; 2) an anti-CD137/4-IBB antibody and wildtype IFN-β-1b molecule; and 3) an anti-CD137/4-IBB antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD137/4-IBB antibody comprised the heavy chain variable region amino acid sequence and light chain variable region amino acid sequence depicted in SEQ ID NO: 11 and SEQ ID NO: 12, respectfully.

The various fusion molecules were then tested in the various in vitro functional assays described in Example 2 to identify anti-CD137/4-IBB-IFN fusion molecules possessing the best activity to impair functions of activated T cells. The best performers were then assessed in vivo for killing activated T cells which express the antigen to which the Ab portion of the fusion molecule binds.

Example 9

In this example, a fusion molecule comprising: 1) an anti-CD278/ICOS antibody and wildtype IFN-β-1a molecule; 2) an anti-CD278/ICOS antibody and wildtype IFN-β-1b molecule; and 3) an anti-CD278/ICOS antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD278/ICOS antibody comprised the heavy chain variable region amino acid sequence and light chain variable region amino acid sequence depicted in SEQ ID NO: 13 and SEQ ID NO: 14, respectfully.

The various fusion molecules were then tested in the various in vitro functional assays described in Example 2 to identify anti-CD278/ICOS-IFN fusion molecules possessing the best activity to impair functions of activated T cells. The best performers were then assessed in vivo for killing activated T cells which express the antigen to which the Ab portion of the fusion molecule binds.

Example 10

In this example, a fusion molecule comprising: 1) an anti-CD279/PD-1 antibody and wildtype IFN-β-1a molecule; 2) an anti-CD279/PD-1 antibody and wildtype IFN-β-1b molecule; and 3) an anti-CD279/PD-1 antibody and wildtype IFN-α molecule were constructed as depicted in FIG. 1 and as described in Example 1. In the fusion molecule constructs of this embodiment, the wildtype IFN-β-1a molecule comprised the amino acid sequence depicted in SEQ ID NO: 17, the wildtype IFN-β-1b molecule comprised the amino acid sequence depicted in SEQ ID NO: 18, and the wildtype IFN-α molecule comprised the amino acid sequence depicted in SEQ ID NO: 19. Constructs were made using the peptide linker SGGGGS (SEQ ID NO: 20), and constructs were made using the peptide linker AEAAAKEAAAKAGS (SEQ ID NO: 21). The anti-CD279/PD-1 antibody comprised the heavy chain variable region amino acid sequence and light chain variable region amino acid sequence depicted in SEQ ID NO: 15 and SEQ ID NO: 16, respectfully.

The various fusion molecules were then tested in the various in vitro functional assays described in Example 2 to identify anti-CD279/PD-1-IFN fusion molecules possessing the best activity to impair functions of activated T cells. The best performers were then assessed in vivo for killing activated T cells which express the antigen to which the Ab portion of the fusion molecule binds.

Importantly, the Ab-IFN fusion molecules described above, and others taught in the present specification will combine the specificity of the antibodies to the target antigen with the potent cytotoxic effects of the IFN molecule, thus sparing non-targeted cells, reducing the systemic toxicity of IFN, improving the on-target effects and the activity of the antibody, and resulting in a local pro-apoptosis signal induced by the IFN. In other words, the Ab-IFN fusion molecules will have at least three major advantages as compared with non-fused IFN: 1) the fusion molecules have reduced IFN activity which addresses the adverse effects of non-fused IFN; 2) the potent cytotoxic effects (induced apoptosis and programmed cell death) of IFN is concentrated at the activated T cells by the fusion molecule (as compared with non-fused IFN); and 3) the IFN part of the fusion molecule does not have cytotoxic effects on healthy cells, including those cells which express the targeted antigen to which the antibody binds. The fusion molecules of the present invention thus provide for monoclonal antibody/IFN-based therapies having superior efficacy and safety profile for the treatment of autoimmune diseases.

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A genetically engineered fusion molecule comprising an interferon (IFN) molecule attached to an antibody (Ab) which targets a CD70 antigen which is differentially expressed on activated T cells, wherein the fusion molecule when contacted to an activated T cell results in induced apoptosis and programmed cell death of said activated T cell, wherein the IFN molecule is selected from the group consisting of an IFN-alpha molecule having the amino acid sequence set forth in SEQ ID NO: 19; an IFN-beta molecule having the amino acid sequence set forth in SEQ ID NO: 17 or SEQ ID NO: 18; and an IFN-alpha mutant molecule, wherein the mutation is selected from the group consisting of H57Y, E58N, Q61S, H57S, E58S, E57A, E58A, Q61A, R149A, R162A, L30A, D35E, E165D, L26A, F27A, L135A, and A145A of SEQ ID NO: 19 and combinations thereof.

2. A fusion molecule of claim 1 wherein said antibody is an antibody selected from a fully human antibody, a humanized antibody, a chimeric antibody, a monoclonal antibody, a polyclonal antibody, a recombinant antibody, an antigen-binding antibody fragment, Fab, Fab', $Fab_2$, $Fab'_2$, IgG, IgM, IgA, IgE, scFv, dsFv, dAb, nanobodies, unibodies, and diabodies.

3. A fusion molecule of claim 2 wherein said antibody is fully human antibody.

4. A fusion molecule of claim 2 wherein said antibody is a humanized antibody.

5. A fusion molecule of claim 1 wherein said interferon is attached to said antibody via a proteolysis resistant peptide linker.

6. A fusion molecule of claim 5 wherein the sequence of said proteolysis resistant peptide linker is selected from SEQ ID NO: 20 and SEQ ID NO: 21.

7. A fusion molecule of claim 1 wherein said fusion molecule is a recombinantly expressed fusion molecule.

8. A composition comprising a fusion molecule of claim 1 in a pharmaceutically acceptable carrier.

9. A composition of claim 8, wherein said composition is formulated for administration via a route selected from subcutaneous, intraperitoneal, intramuscular, intrasternal, intravenous, intraarterial, intrathecal, intraventricular, intraurethral.

* * * * *

SEQUENCE LISTING

<160> NUMBER OF SEQ ID NOS: 21

<210> SEQ ID NO 1
<211> LENGTH: 137
<212> TYPE: PRT
<213> ORGANISM: Artificial Sequence
<220> FEATURE:
<223> OTHER INFORMATION: anti-CD70 Ab heavy chain variable region

<400> SEQUENCE: 1

Met Ala Trp Val Trp Thr Leu Leu Phe Leu Met Ala Ala Ala Gln Ser
1               5                   10                  15

Ala Gly Ala Gln Ile Gln Leu Val Gln Ser Gly Pro Glu Val Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Glu Thr Ser Ala Ser
                85                  90                  95

Thr Ala Tyr Leu Gln Ile Asn Asn Leu Lys Asn Gly Asp Thr Ala Thr
            100                 105                 110

Tyr Phe Cys Ala Arg Asp Tyr Gly Asp Tyr Gly Met Asp Tyr Trp Gly
        115                 120                 125

Gln Gly Thr Ser Val Thr Val Ser Ser
    130                 135

<210> SEQ ID NO 2
<211> LENGTH: 132
<212> TYPE: PRT
<213> ORGANISM: Artificial Sequence
<220> FEATURE:
<223> OTHER INFORMATION: anti-CD70 Ab light chain variable region

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys

```
            100                 105                 110

Gln His Ser Arg Glu Val Pro Trp Thr Phe Gly Gly Gly Thr Lys Leu
        115                 120                 125

Glu Ile Lys Arg
    130


<210> SEQ ID NO 3
<211> LENGTH: 117
<212> TYPE: PRT
<213> ORGANISM: Artificial Sequence
<220> FEATURE:
<223> OTHER INFORMATION: anti-CD30 Ab heavy chain variable region

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115


<210> SEQ ID NO 4
<211> LENGTH: 111
<212> TYPE: PRT
<213> ORGANISM: Artificial Sequence
<220> FEATURE:
<223> OTHER INFORMATION: anti-CD30 Ab light chain variable region

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110


<210> SEQ ID NO 5
<211> LENGTH: 120
<212> TYPE: PRT
<213> ORGANISM: Artificial Sequence
<220> FEATURE:
```

<223> OTHER INFORMATION: anti-CD40L/CD154 Ab heavy chain variable region

<400> SEQUENCE: 5

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Asn Gly
            20                  25                  30

Phe Trp Ile Trp Ile Arg Lys Pro Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Ser Arg Asp Thr Ser Lys Asn Gln Phe Ser Leu
65                  70                  75                  80

Lys Leu Ser Ser Val Thr Ala Ala Asp Thr Gly Val Tyr Tyr Cys Ala
                85                  90                  95

Cys Arg Ser Tyr Gly Arg Thr Pro Tyr Tyr Phe Asp Phe Trp Gly Gln
            100                 105                 110

Gly Thr Thr Leu Thr Val Ser Ser
        115                 120
```

<210> SEQ ID NO 6
<211> LENGTH: 107
<212> TYPE: PRT
<213> ORGANISM: Artificial Sequence
<220> FEATURE:
<223> OTHER INFORMATION: anti-CD40L/CD154 Ab light chain variable region

<400> SEQUENCE: 6

```
Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asn Val Ile Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Tyr
                85                  90                  95

Thr Phe Gly Gly Gly Thr Lys Leu Glu Ile Lys
            100                 105
```

<210> SEQ ID NO 7
<211> LENGTH: 127
<212> TYPE: PRT
<213> ORGANISM: Artificial Sequence
<220> FEATURE:
<223> OTHER INFORMATION: anti-CD25 Ab heavy chain variable region

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Asn Trp Val Arg Gln Ala Pro Gly Gln Gly Leu Glu Trp Met
        35                  40                  45

Gly Arg Ile Ile Pro Ile Leu Asp Ile Ala Asp Tyr Ala Gln Lys Phe
```

```
    50                  55                  60

Gln Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Asp Trp Phe Asp Pro Trp Gly Gln Gly Thr Leu Val Thr
            100                 105                 110

Val Ser Ser Ala Ser Thr Lys Gly Pro Ser Val Phe Pro Leu Ala
        115                 120                 125


<210> SEQ ID NO 8
<211> LENGTH: 120
<212> TYPE: PRT
<213> ORGANISM: Artificial Sequence
<220> FEATURE:
<223> OTHER INFORMATION: anti-CD25 Ab light chain variable region

<400> SEQUENCE: 8

Glu Asn Val Leu Thr Gln Ser Pro Gly Thr Leu Ser Leu Ser Pro Gly
1               5                   10                  15

Glu Arg Ala Thr Leu Ser Cys Arg Ala Ser Gln Ser Gly Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro
        115                 120


<210> SEQ ID NO 9
<211> LENGTH: 119
<212> TYPE: PRT
<213> ORGANISM: Artificial Sequence
<220> FEATURE:
<223> OTHER INFORMATION: anti-CD134/OX40 Ab heavy chain variable region

<400> SEQUENCE: 9

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ser Met
            20                  25                  30

Asn Trp Val Arg Gln Ala Pro Gly Lys Gly Leu Glu Trp Val Ser Tyr
        35                  40                  45

Ile Ser Ser Ser Ser Ser Thr Ile Tyr Tyr Ala Asp Ser Val Lys Gly
    50                  55                  60

Arg Phe Thr Ile Ser Arg Asp Asn Ala Lys Asn Ser Leu Tyr Leu Gln
65                  70                  75                  80

Met Asn Ser Leu Arg Asp Glu Asp Thr Ala Val Tyr Tyr Cys Ala Arg
                85                  90                  95

Gly Val Tyr His Asn Gly Trp Ser Phe Phe Asp Tyr Trp Gly Gln Gly
            100                 105                 110
```

```
Thr Leu Leu Thr Val Ser Ser
        115


<210> SEQ ID NO 10
<211> LENGTH: 110
<212> TYPE: PRT
<213> ORGANISM: Artificial Sequence
<220> FEATURE:
<223> OTHER INFORMATION: anti-CD134/OX40 Ab light chain variable region

<400> SEQUENCE: 10

Arg Cys Asp Ile Gln Met Thr Gln Ser Pro Ser Ser Leu Ser Ala Ser
1               5                   10                  15

Val Gly Asn Arg Val Thr Ile Thr Cys Arg Ala Ser Gln Asp Ile Ser
            20                  25                  30

Ser Trp Leu Ala Trp Tyr Gln Gln Lys Pro Glu Lys Ala Pro Lys Ser
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Asn Ser Tyr
                85                  90                  95

Pro Leu Thr Phe Gly Gln Gly Thr Arg Leu Glu Ile Lys Arg
            100                 105                 110


<210> SEQ ID NO 11
<211> LENGTH: 121
<212> TYPE: PRT
<213> ORGANISM: Artificial Sequence
<220> FEATURE:
<223> OTHER INFORMATION: anti-CD137/4-1BB Ab heavy chain variable region

<400> SEQUENCE: 11

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120


<210> SEQ ID NO 12
<211> LENGTH: 109
<212> TYPE: PRT
<213> ORGANISM: Artificial Sequence
<220> FEATURE:
<223> OTHER INFORMATION: anti-CD137/4-1BB Ab light chain variable region

<400> SEQUENCE: 12

Glu Ile Val Leu Thr Gln Ser Pro Ala Thr Leu Ser Leu Ser Pro Gly
```

-continued

```
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105


<210> SEQ ID NO 13
<211> LENGTH: 98
<212> TYPE: PRT
<213> ORGANISM: Artificial Sequence
<220> FEATURE:
<223> OTHER INFORMATION: anti-CD278/ICOS Ab heavy chain variable region

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg


<210> SEQ ID NO 14
<211> LENGTH: 94
<212> TYPE: PRT
<213> ORGANISM: Artificial Sequence
<220> FEATURE:
<223> OTHER INFORMATION: anti-CD278/ICOS Ab light chain variable region

<400> SEQUENCE: 14

Asp Ile Gln Met Thr Gln Ser Pro Ser Ser Val Ser Ala Val Ser Gly
1               5                   10                  15

Asp Arg Val Thr Ile Thr Cys Arg Ala Ser Gln Gly Ile Ser Arg Leu
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Gly Asp Phe Ala Thr Tyr Tyr Cys Gln Gln Ala Asn Ser Phe
                85                  90
```

-continued

<210> SEQ ID NO 15
<211> LENGTH: 119
<212> TYPE: PRT
<213> ORGANISM: Artificial Sequence
<220> FEATURE:
<223> OTHER INFORMATION: anti-CD279/PD-1 Ab heavy chain variable region

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Gly Leu Arg Ser Leu Arg Ser Asp Asp Thr Ala Val Tyr Tyr Cys
                85                  90                  95

Ala Arg Asp Ala Asp Tyr Ser Ser Gly Ser Gly Tyr Trp Gly Gln Gly
            100                 105                 110

Thr Leu Val Thr Val Ser Ser
        115
```

<210> SEQ ID NO 16
<211> LENGTH: 108
<212> TYPE: PRT
<213> ORGANISM: Artificial Sequence
<220> FEATURE:
<223> OTHER INFORMATION: anti-CD279/PD-1 Ab light chain variable region

<400> SEQUENCE: 16

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Met Val Ile Tyr
        35                  40                  45

Lys Asp Thr Gly Arg Pro Ser Gly Ile Pro Glu Arg Phe Ser Gly Ser
    50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105
```

<210> SEQ ID NO 17
<211> LENGTH: 166
<212> TYPE: PRT
<213> ORGANISM: Artificial Sequence
<220> FEATURE:
<223> OTHER INFORMATION: human interferon beta 1a wildtype protein

<400> SEQUENCE: 17

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30
```

```
Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165


<210> SEQ ID NO 18
<211> LENGTH: 166
<212> TYPE: PRT
<213> ORGANISM: Artificial Sequence
<220> FEATURE:
<223> OTHER INFORMATION: human interferon beta 1b wildtype protein

<400> SEQUENCE: 18

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165


<210> SEQ ID NO 19
<211> LENGTH: 165
<212> TYPE: PRT
<213> ORGANISM: Artificial Sequence
<220> FEATURE:
<223> OTHER INFORMATION: human interferon alpha 2 wildtype protein
```

-continued

<400> SEQUENCE: 19

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 20
<211> LENGTH: 6
<212> TYPE: PRT
<213> ORGANISM: Artificial Sequence
<220> FEATURE:
<223> OTHER INFORMATION: peptide linker

<400> SEQUENCE: 20

```
Ser Gly Gly Gly Gly Ser
1               5
```

<210> SEQ ID NO 21
<211> LENGTH: 14
<212> TYPE: PRT
<213> ORGANISM: Artificial Sequence
<220> FEATURE:
<223> OTHER INFORMATION: peptide linker

<400> SEQUENCE: 21

```
Ala Glu Ala Ala Ala Lys Glu Ala Ala Ala Lys Ala Gly Ser
1               5                   10
```